(12) United States Patent
Liu et al.

(10) Patent No.: US 9,637,725 B2
(45) Date of Patent: May 2, 2017

(54) POLYPEPTIDES HAVING CATALASE ACTIVITY AND POLYNUCLEOTIDES ENCODING SAME

(71) Applicant: Novozymes Inc.

(72) Inventors: Ye Liu, Beijing (CN); Junxin Duan, Beijing (CN); Yu Zhang, Beijing (CN); Lan Tang, Beijing (CN)

(73) Assignee: Novozymes Inc., Davis, CA (US)

( * ) Notice: Subject to any disclaimer, the term of this patent is extended or adjusted under 35 U.S.C. 154(b) by 0 days.

(21) Appl. No.: 14/366,127

(22) PCT Filed: Dec. 19, 2012

(86) PCT No.: PCT/CN2012/086946
§ 371 (c)(1),
(2) Date: Jun. 17, 2014

(87) PCT Pub. No.: WO2013/091547
PCT Pub. Date: Jun. 27, 2013

(65) Prior Publication Data
US 2014/0335572 A1 Nov. 13, 2014

Related U.S. Application Data

(60) Provisional application No. 61/582,913, filed on Jan. 4, 2012.

(30) Foreign Application Priority Data

Dec. 19, 2011 (CN) .................. PCT/CN2011/084230

(51) Int. Cl.
*C12P 1/00* (2006.01)
*C12P 19/02* (2006.01)
*C12N 9/08* (2006.01)
*C12P 3/00* (2006.01)
*D06L 3/11* (2006.01)

(52) U.S. Cl.
CPC .............. *C12N 9/0065* (2013.01); *C12P 3/00* (2013.01); *C12P 19/02* (2013.01); *D06L 3/11* (2013.01); *C12Y 111/01006* (2013.01)

(58) Field of Classification Search
None
See application file for complete search history.

(56) References Cited

U.S. PATENT DOCUMENTS

2010/0330646 A1  12/2010  Okakura et al.
2013/0309723 A1* 11/2013  Huang ................. C12N 9/0065
                                         435/72

FOREIGN PATENT DOCUMENTS

| JP | 2004261137 A | 9/2004 |
| JP | 2007143405 A | 6/2007 |
| WO | 92/17571 A1 | 10/1992 |
| WO | WO 2010/080408 A2 * | 7/2010 |
| WO | 2012130120 A1 | 10/2012 |

OTHER PUBLICATIONS

Calera et al,—Genbank Access No. AAB 712 23 (2000).
Chance Maehly et al, Methods Enzymol, vol. 2, pp. 764-791 (1955).
Fedorova et al,—Uniprot Access No. A1DJU9 (2007).
Janto et al,—Uniprot Acces No. P30266 (1993).
Liu et al, Chem Bioeng, vol. 26, No. 3, pp. 15-18 (2009).
Yoshida et al,—Uniprot Access No. P42234 (1995).

* cited by examiner

*Primary Examiner* — David J Steadman
(74) *Attorney, Agent, or Firm* — Kelly Reynolds

(57) ABSTRACT

Provided are isolated polypeptides having catalase activity and polynucleotides encoding the polypeptides. Also provided are nucleic acid constructs, vectors and host cells comprising the polynucleotides as well as methods of producing and using the polypeptides.

20 Claims, 10 Drawing Sheets

```
        M   P   N   L   V   R   L   L   A   L   A   G   V   V   S   A   A   C   P   Y
   1  atgccgaacctcgtacggctccttgctcttgcgggagtcgtgtcggccgcttgtccctac
        L   S   G   E   L   D   K   R   Q   A   D   S   S   N   D   A   A   Q   A   T
  61  ctttcagggaattggacaagcgtcaggctgactcgagcaacgatgcagctcaggctact
        E   E   F   L   Q   Q   F   Y   L   N   D   N   D   T   Y   M   T   T   D   T
 121  gaggaatttctccagcagttctatctcaacgacaatgatacatatatgactactgacact
        G   T   P   I   A   D   Q   Q   S   L   S   V   G   E   R   G   P   T   L   L
 181  ggcacccccattgctgaccagcagagcttaagcgtgggtgagagaggcccaacgctcctt
        E   D   F   I   F   R   Q   K   I   Q   R   F   D   H   E   R
 241  gaggactttatcttccgccagaaaatacagcgatttgaccatgagcgtGTATGTGACAAA 301  ATCATGTGCCTTGCCGCATACTCTCTCGTCCGTCACAGATATGGCTAACGTGCCGTCGAA
                    V   P   E   R   A   V   H   A   R   G   A
 361  TTGATACAGgttcctgaacgtgctgtgcacgcacgcggagctgGTATGATGCCACATTCC
                                                                G   A   H
 421  TTGTAACCCACCGTTCAGAAGTTAATGCTAAATGGCACTTTTTCGACAATAGgcgcccat
        G   V   F   T   S   Y   G   D   F   S   N   I   T   A   A   S   F   L   S   A
 481  ggagttttcacatcgtacggagacttctcgaacatcactgctgcttcgttcctgtccgcg
        E   G   K   Q   T   P   V   F   V   R   F   S   T   V   A   G   S   R   G   S
 541  gaaggcaaacagactcctgtatttgtccgttttccacggttgctggaagccgtggtagc
        S   D   M   A   R   D   V   H   G   F   A   T   R   F   Y   T   D   E   G   N
 601  tctgacatggctcgagacgtccatggttttgcaactcgattctatactgacgaaggcaac
        F
 661  tttgGTAAGTCCTCTCTCTTGGGCGAGGATGGTCAATGGTATAGCACGTTTGATTGACTT
                        D   I   V   G   N   N   I   P   V   F   F   I   Q   D   A
 721  TAATTGGTACCCGCAGatatcgtcggaaacaacatcccggtgttcttcatccaggacgct
        I   Q   F   P   D   L   I   H   A   V   K   P   K   Q   D   N   E   I   P   Q
 781  atccaatcccggaccttatccacgccgtgaagccaaagcaagataatgagatccctcaa
        A   A   T   A   H   D   S   A   W   D   F   F   S   Q   Q   P   S   T   M   H
 841  gcagccaccgcccacgattctgcttgggacttcttcagccagcagcccagcacgatgcat
        T   L   M   W   A   M   A   G   H   G   I   P   R   S   Y   R   H   M   D   G
 901  accttgatgtgggcaatggcaggacacggcatcccacgttcataccgacacatggacggg
        F   G   V   H   T   F   R   F   V   T   D   E   G   Q   S   K   L   V   K   F
 961  tttggtgtgcacaccttccgttttgtgactgacgaggacagtcgaagcttgtcaagttc
        H   F   K   T   L   Q   G   R   A   S   M   V   W   E   E   A   Q   V   I   S
1021  cacttcaagaccttgcaaggaagggcttctatggttgggaagaggcacaagtcatctcg
        G   K   N   T   D   F   H   R   Q   D   L   F   E   A   I   E   S   G   T   Y
1081  gggaagaatacagattttcatagacaggacctctttgaggcaattgagtccgggacttat
        P   E   W   E
1141  ccagagtgggagGTATGCATCTGCATTTCCATCCTCTCTTAGCCTTTTCTTGGGTCCCAG
                        F   G   V   Q   I   V   D   E   E   D   E   L   K
1201  GTGCTGACCTTTGTGTACAGttcggtgtccaaattgttgatgaggaagatgagttgaaat
        F   G   F   D   L   L   D   P   T   K   I   I   P   E   D   L   V   P   V   T
1261  ttggattcgacttgctcgacccaaccaagatcatccctgaggacttggttcccgtcacac
        P   L   G   K   L   Q   L   N   R   N   P   R   N   Y   F   A   E   T   E   Q
1321  cgttgggaaagctccagttgaaccggaaccctcgcaactactttgctgaaactgagcagg
        V   M
1381  ttatgGTATGTCTTGCATTTCGGTGAAATGCATTCTCGTTGGCCGTACCGAGAGTCTAAC
                        F   Q   P   G   H   I   V   R   G   I   D   F   T   D   D
1441  GAATTTTTGTTTATAGttccaacctggtcacattgtccgtggaatcgatttcacagatga
        P   L   L   Q   G   R   L   F   S   Y   L   D   T   Q   L   N   R   H   G   G
1501  tcctctgctccaaggccgactgttctcctaccttgacactcagctgaacaggcatggtgg
        P   N   F   E   Q   L   P   I   N   Q   P   R   V   P   I   H   N   N   N   R
1561  accaaatttcgagcagctccctatcaaccagcctcgagtccctatccacaacaacaatcg
        D   G   A
1621  tgatggtgccgGTAGGTTTGATCAATCCTTGTGGCGATCCATTTCCCTTGCTGTCAATGT
                        G   Q   M   Y   I   P   L   N   P   H   A   Y   S
1681  TTCTAACTTTGTTTCGAAACAGgtcaaatgtacattcctctgaacccccatgcgtatagt
```

Fig. 1

```
              P  N  T  L  H  A  S  S  P  R  Q  A  N  E  T  H  G  K  G  F
     1741  cccaatactctccacgctagttcccctcggcaagccaacgagacccacggcaaaggtttc
              F  T  T  P  G  R  T  P  S  G  T  L  Q  R  S  L  S  P  T  F
     1801  ttcactaccccctggacgcactccatctggcactctgcaacgatctctcagccctacattt
              A  D  V  W  S  Q  P  R  L  F  Y  N  S  L  H  P  V  E  R  Q
     1861  gcggatgtatggtctcagccacgtctcttctacaactcactacatcctgtggaacgccaa
              F  L  V  N  A  I  R  F  E  T  S  N  L  A  S  S  V  V  R  K
     1921  ttcctggtgaacgcgatcaggttcgagacgtcaaatctagccagctcggtcgtacgcaag
              N  V  I  I  Q  L  N  R  I  S  N  D  L  A  R  R  V  A  R  F
     1981  aatgtgatcatccagctcaaccgaatttccaacgacctggcgagacgcgtggcacggttt
              I  G  V  E  E  P  Q  P  D  E  K  F  Y  H  N  N  K  T  V  P
     2041  atcggcgttgaggaacctcagcctgatgaaaagttctaccacaacaacaagacagtgccg
              L  G  T  F  G  T  P  L  K  S  L  A  G  L  K  I  G  I  L  S
     2101  cttggtactttcggaaccccgttgaagtcgcttgctggtctgaagattggtattctctcc
              S  V  N  S  Y  E  E  A  S  R  I  K  S  A  L  L  E  K  D  S
     2161  agtgtgaacagctacgaggaggcgtcgcgcatcaagagtgcgttgcttgaaaaggactcg
              S  V  K  V  S  V  V  A  E  R  L  V  P  G  E  E  G  T  V  A
     2221  agcgtcaaggtgtctgtcgtcgcggagagattggttcccggggaggagggcacagtggcc
              Y  T  A  A  D  G  T  S  F  D  G  I  I  V  S  N  G  T  A  D
     2281  tacaccgcagctgatggaacttcttttcgacggtatcattgtgtcaaacggcacggcggat
              G  F  T  P  Y  A  S  S  P  L  F  P  A  G  R  P  L  Q  I  L
     2341  ggtttcaccccgtatgcctcgtctccgctcttcccggctggccggccactgcagatcctc
              V  D  A  Y  R  Y  G  K  P  V  G  A  I  G  D  A  G  L  K  A
     2401  gttgacgcatatcgctacggcaagcctgttggtgctattggagatgctggactcaaggcc
              L  D  N  A  G  I  Q  E  A  E  R  D  A  E  K  G  V  F  T  A
     2461  ctcgacaatgctggtatccaagaagctgagcgtgatgcggagaagggtgtgttcacagcg
              S  D  A  D  A  T  F  V  E  D  F  L  D  G  L  K  V  F  R  F
     2521  tctgacgccgatgcaaccttcgtcgaggactttctcgatggattgaaggtgttccgattc
              L  E  R  F  D  I  D  E  D  A  E  D  Y  *
     2581  cttgagcggtttgatattgacgaagatgcagaggactactag
```

Fig. 1 continued

```
           M  R  L  G  A  L  A  N  L  L  V  L  S  Q  L  A  F  V  R  G
    1  atgcgactaggtgccttggcaaaccttctcgtcctctcccagttagcctttgtaagaggc
           D  D  D  R  S  N  N  V  C  A  F  Q  E  P  V  S  G  V  G  A
   61  gacgatgatcgcagcaacaacgtctgtgccttccaagaaccagtatctggagttggagcc
           N  A  K  T  E  Q  L  K  L  F  T  I  N  D  E  G  T  R  E  T
  121  aatgcaaagaccgagcagctcaaactcttcaccattaatgacgagggcactcgggagaca
           T  N  F  G  V  L  V  N  N  S  D  S  L  K  A  G  Y  R  G  P
  181  accaactttggtgtcttggtcaacaatagcgatagcttgaaggcgggctaccgcggccct
           T  L  M  E  D  F  M  L  R  E  K  I  M  H  F  G  K
  241  accctaatggaagactttatgttgcgggaaaagataatgcactttggcaaGTAAAAATCT 301  GTACAAAAATAAAAAGCAAAGGATACTAACGTTCAAGCTGCATCCTTATAGATCATGAAA
                                                                 I  P
  361  GGTAGCTACTATACTGCTGATGAAGAAAATGCATATAATTAACCTCTCTATCAGaattcc
           E  R  V  V  H  A  R  G  V  A  A  H  G  Y  F  E  S  Y  A  D
  421  tgaacgcgttgtacacgctcgaggtgtagctgcccacggctactttgaatcatatgccga
           W  S  S  L  T  A  A  K  F  L  S  A  P  G  K  Q  T  P  T  F
  481  ctggtcaagtctcacagcagccaagttcctgagcgctccaggaaagcagacacctacctt
           V  R  F  S  P  V  L  G  S  K  G  S  A  D  T  V  R  D  D  R
  541  tgtccgattctctcccgtgctaggcagcaaaggttccgcggacactgttcgcgatgatcg
           G  F  A  T  R  F  Y  T  E  E  G  N  F  D  L
  601  tggtttcgctacacgcttctacaccgaagaaggcaatttcgatctagGTGATGCATAGTC
                                                      V  G  N
  661  TATTGCTACAAGCCTGCATCGAACCTGTCTCTCATTCAATTTATTCAATAGttggcaaca
           I  I  A  P  F  F  V  Q
  721  ttattgctccattctttgtccaagGTATGTTTAAGCAAACGATGAAAACCTTTCGAGTGA
                                                   D  A  I  K  F  P  D
  781  TGATTCTGATTGATATTTAAATGCATATATCCTCAAAATAGatgctatcaagtttcctga
           L  I  H  A  A  K  P  Q  P  D  T  N  V  P  Q  A  S  T  A  H
  841  tcttattcatgccgcaaaaccacaaccagatactaatgtgccgcaagcatcaaccgctca
           E  T  A  Y  D  F  F  S  T  F  P  E  S  I  H  T  V  L  W  V
  901  cgaaacggcgtatgactttttcagtacgttcccagagtccatacacacagttctctgggt
           L  S  G  R  I  P  R  S  L  R  Q  V  E  G  F  G  I  H  T
  961  gctttctggacgtggcattccccgcagcctccgccaagtcgaaggatttggtatccacac 1021  GTAAGTATCCATGTTTTTGCAATTAGTACACTTTTGCAATATCCCTAACAATTCCTATCC
            F  R  L  V  N  E  K  G  E  G  T  F  V  K  F  I  W
 1081  GTTATAGtttccgtcttgtcaatgagaaaggcgagggtacgtttgtcaagtttatctgga
           K  P  H  Q  G  L  S  N  L  A  W  A  S
 1141  aaccacatcaaggtctttcgaatcttgcttgggcaagtGTTCAATATTCGTGGTATTTGA
                                                   P  E  A  Q  K  I  S  G
 1201  CATCGGAAAATGCATTTGCTAACATTAATTAAACAGccagaagcacaaaaaatcagtggg
           I  N  P  D  F  H  H  V  D  L  T  T  A  I  E  R  G  D  Y  P
 1261  attaacccggatttccaccacgttgatttgactactgctatcgaacgaggagattatccg
           V  Y  D  L  C  V  Q  I  I  P  E  E  D  E  F  K  F  D  F  D
 1321  gtttacgatctctgcgtccaaatcatacccgaggaggacgaatttaaattcgatttcgat
           L  L  D  P  T  K  I  V  P  E  S  I  V  P  V  T  R  L  G  K
 1381  ttactcgaccccaccaagattgtacctgagtccatagtaccagtcaccaggctcggaaag
           L  V  L  N  R  K  V  D  N  F  F  S  E  T  E  Q  V  T  Y  H
 1441  ctggtactcaaccggaaagtcgataacttcttttcagaaacggagcaagtaacttaccac
           A  G  H  I  V  R
 1501  gcaggccacattgttcgagGTATGATTTATTTGACAACAAAATTTTGCACCACCAGCGGT
                                G  I  G  F  T  D  D  P  L  L  Q
 1561  GATTTCTAACGACGTCTTCGTGGCAACAGgcatcggctttacagatgatcccttgctcca
           G  R  L  F  S  Y  L  D  T  Q  L  N  R  M  S  S  A  N  F  L
 1621  aggccgtctctttagctacttggatacacagcttaatcgcatgagctcagctaatttcct
           Q  L  P  I  N  R  P  I  T  P  V  H  N  N  Q  R
 1681  ccagctgcctatcaatcgaccgattactccagtgcacaataaccagcgGTATCAACAACT
```

Fig. 2

```
                                                                    D   G   F   M
1741  TGAACGATATCTAACGAGTCAACCGACTTATTTTGCTTTTGTCCAGggacggtttcatgc
        Q   Y   N   V   Y   K   G   A   V   A   Y   F   P   S   S   I   G   K   P   P
1801  agtacaatgtgtacaagggtgccgtagcctacttcccgagctcaataggcaaacctccag
        E   V   T   P   P   E   Q   G   G   Y   I   E   Y   P   E   K   V   N   G   I
1861  aagtgacgcctccggagcaaggtggctacattgaatatcccgaaaaagtcaatggtatca
        K   V   R   G   R   S   P   S   F   F   D   F   Y   S   H   A   Q   L   F   W
1921  aagttcgcggccggtctccaagcttctttgacttttactcgcatgcacagctgttctgga
        N   S   L   T   E   A   E   Q   Q   Q   L   V   D   A   S   R   F   E   L   G
1981  actcgctcacagaagctgagcagcagcagctcgtggacgccagtcgtttcgagctcggca
        K   S   Q   S   M   E   V   R   K   R   M   I   D   V   L   N   H   V   D   N
2041  agtctcagtcgatggaagtccgcaaacgaatgattgatgttttgaaccacgtcgacaatg
        G   L   A   R   R   V   A   V   G   I   G   L   E   P   P   E   K   L   Y   E
2101  gtctcgcgcgacgcgtcgctgtgggtatcggcctcgagccgcccgaaaagttgtacgaaa
        N   Q   N   K   T   S   V   G   L   S   I   E   K   Y   P   K   P   D   N   I
2161  accaaaacaagacgagtgttggcttgtccattgaaaagtatccaaaaccggacaatatcc
        R   T   R   T   V   A   I   L   T   A   P   G   T   N   T   H   E   A   Q   A
2221  gcactcgcactgtggccatcttgacagcaccaggcacaaacactcacgaagctcaagcca
        M   Y   D   Y   L   K   Q   E   G   A   Y   P   E   Y   I   G   I   H   L   G
2281  tgtacgactatctcaagcaggagggcgcttatcccgagtatatcggcatccatctaggaa
        K   Q   D   G   L   N   I   T   N   T   Y   L   T   A   S   S   V   L   Y   D
2341  aacaggacggtctcaatattacaaacacatatttgaccgcatcttctgtgctctacgacg
        A   L   Y   V   P   G   G   K   E   G   I   G   R   L   T   K   P   S   S   L
2401  ctctctatgttccgggtggcaaagaaggaattggcagactcacgaaaccttcgagtctat
        F   P   Y   E   E   P   K   V   W   L   L   D   A   W   R   H   G   K   P   I
2461  tcccgtatgaggagcccaaggtttggctgctggatgcctggagacacggcaaacctatca
        S   A   S   G   E   G   I   K   L   L   K   A   S   D   V   K   I   P   K   V
2521  gcgcgtcaggcgaaggcatcaagctgctcaaggcttccgatgtcaagattcccaaagtca
        K   E   N   E   V   T   E   A   Q   G   V   I   V   G   P   P   G   D   D   L
2581  aagaaaatgaggtcacagaggcgcaaggagttatcgtgggtccacctggggatgacttga
        N   Q   K   Y   R   S   A   L   V   Q   Q   R   F   W   Y   R   L   P   M   D
2641  atcagaagtaccgctcggcacttgtacagcagcgcttctggtatcgattaccaatggatc
        P   P   I   *
2701  ctcccatttaa
```

Fig. 2 continued

```
       M  K  A  G  S  L  L  G  I  V  A  S  V  A  L  L  L  Q  Q  Q
   1 atgaaagccggttcgcttctcggaattgttgcaagcgttgcactcttgctccagcagcaa
       V  A  F  A  E  E  T  C  A  F  Q  N  P  V  G  D  N  S  E  D
  61 gtagcttttgctgaagaaacatgcgcttttcaaaaccctgttggtgataacagcgaagat
       A  K  A  A  Q  L  K  A  F  T  R  N  D  A  G  T  Q  E  T  T
 121 gcgaaagccgcccagctcaaggcttttcacacgcaacgacgctggcactcaagaaactacg
       N  F  G  Q  L  V  N  N  T  D  S  L  K  A  G  L  R  G  P  T
 181 aactttggtcagcttgtaaacaacacggacagtttgaaggctggtttgcgcggccctaca
       L  L  E  D  F  M  M  R  E  K  I  M  H  F
 241 ctgcttgaagactttatgatgcgtgaaaagatcatgcactttgGTACGTATTATTGTATC
                                                                D  H
 301 TAAACCTTCAATTGATTTTGTATTTATTGTAACCGTGCAATTATCTTTCGTGTAGaccat
       E  R  I  P  E  R  A  V  H  A  R  G  V  G  A  H  G  Y  F  E
 361 gaacgaattcccgagcgcgcggtacacgctcgaggtgtcggtgcccacggctactttgaa
       P  Y  A  D  W  G  N  I  T  A  A  K  F  L  R  E  P  G  K  R
 421 ccctacgctgactggggcaacatcaccgctgccaagttcttgcgtgaacctggcaaaaga
       T  P  V  F  V  R  F  S  T  V  L  G  S  R  G  S  P  D  T  V
 481 acgccggtctttgtgcgattctcgaccgtgcttggttcccgtggctcgcctgacactgtt
       R  D  V  R  G  F  A  T  R  F  Y  T  E  E
 541 cgcgacgttcgcggttttgctactcggttctacaccgaggaggGTTTGTGGGATCTAGGC 601 AAGTTTTTAATTCTTTTTTTCGGTGTAGACAGAAACTTTATTCTTTTTTTCGAGTGCAAGA
                      V  G  N  A  I  A  P  F  F  V  Q
 661 ACTTATAACCGCGTTGTATATAGtcggaaacgccattgcaccgttctttgtacaggGTAA 721 GCTTCCCGATGATAGGATTTGCTGCTTATCCGTGGTGAACATTTGCTGATGACTACTGCT
             D  G  I  K  F  P  D  L  I  H  A  G  K  P  E  P  D
 781 ATTTTACATAGacggtatcaagttcccagacttgatccacgctggcaaaccagagccaga
       K  E  V  P  Q  A  G  T  A  H  E  T  A  Y  D  F  F  A  E  F
 841 caaggaagttcctcaagccggtacagctcacgaaactgcctatgatttcttcgccgaatt
       P  E  T  L  H  T  V  F  W  A  L  S  G  R  G  I  P  R  S  F
 901 cccagaaactttgcacactgttttctgggctctctctggtcgcggtattccgagaagttt
       R  Q  V  E  G  F  G  V  H  T
 961 ccgtcaagttgaaggttttggtgtccatacGTAAGTCTGGATAAACCGATTGCGTTGCTG
                                    F  R  L  I  N  E  E  G  K  S  V
1021 CCCATTTTGCTAACTCCAGACCACCAGAttccgattaatcaacgaggaaggcaagtctgt
       F  V  K  F  H  W  K  P  L  Q  G  L  S  N  L  V  W
1081 gtttgtcaagttccactggaaacctctccagggtctctccaaccttgtttggGTGAGTTA 1141 TTTAAAACAGTCGTTAGTAACACTATGTCAGTAAGCTAATATATAAATCAATCGTTTTGA
             D  E  A  Q  K  I  A  G  K  D  I  D  F  H  R  N  D  L
1201 ACAGgatgaagcgcagaagatagctggaaaggatatcgatttccacagaaacgatctgGT 1261 GAGTCTTGGACATGGACAAAGAAAAATGTTCACCGAATTGTGTGATTAACTATTCTTGTT
                      Y  T  A  I  E  R  G  D  Y  P  E  W  E  L  G  V  Q
1321 ATACGCTCAGtatactgctattgagcgtggcgactatccagaatgggaactcggtgtaca
       I  I  P  E  E  D  E  D  K  F  D  F  D  L  L  D  P  T  K  I
1381 gatcatacctgaggaagacgaagacaagtttgactttgatctcttggacccaccaagat
       V  P  E  S  L  V  P  V  T  R  I  G  K  M  V  L  N  R  N  V
1441 tgttcccgagtctttggttcctgtgacgcgtatcggcaagatggtattaaaccgcaacgt
       N  N  Y  F  S  E  T  E  Q  V  T  F  H  P  G  H  I  V  R  G
1501 taacaactacttttcggagacggagcaagttaccttccaccctggtcacattgttcgcgg
       I  G  F  T  N  D  P  L  L  Q  G  R  L  F  S  Y  L  D  T  Q
1561 tattggctttaccaacgatcctttgcttcaaggccgtctgttcagttacttggacacaca
       L  N  R  M  N  S  A  N  F  M  Q  I  P  I  N  R  P  I  N  A
1621 gttgaacgtatgaactcggccaatttcatgcaaatccccatcaaccgacctatcaacgc
       V  H  N  N  Q
1681 tgtgcacaataaccagGTAAATTTCAATAGGCCTGACTTTCATTGTTACCATTCCCGTAA
```

Fig. 3

```
                                          R  D  G  Y  L  Q  M  N  T  F  T
1741  CTTAACCATGGTATTTCTTGTGAAAAGagggacggctacctccaaatgaacacgtttacc
         G  N  V  A  Y  H  P  N  G  L  Q  R  N  T  P  S  M  V  D  P
1801  ggcaatgtcgcctaccacccgaatggtctccaacgtaacacgccttcgatggtcgaccct
         D  Q  G  G  Y  I  D  Y  P  E  E  I  H  G  K  K  Q  R  G  R
1861  gaccaaggtggatacattgactatccggaggaaatccatggcaaaaagcaacgtggacgc
         S  A  K  F  F  D  Y  Y  S  Q  A  Q  L  F  Y  N  S  L  T  P
1921  agcgccaaattctttgattactactcgcaagctcaactgttctacaactctctgaccccg
         A  E  K  Q  Q  M  I  D  G  L  R  F  E  I  G  K  S  K  S  L
1981  gctgagaagcaacagatgatcgatggtctccgcttcgagataggcaagtccaagtcgctg
         D  V  R  K  R  M  I  N  V  I  N  H  V  D  N  D  L  A  R  R
2041  gacgttcgcaagcgtatgatcaatgtcatcaatcatgtcgataacgaccttgctcgtcgt
         I  A  K  S  I  N  V  P  L  P  E  K  I  V  E  N  K  N  Q  T
2101  atcgctaagtctatcaatgtccccttgcccgaaaaaattgtcgagaacaagaaccagacg
         S  T  G  L  S  I  E  L  Y  P  K  P  D  N  I  R  T  R  T  V
2161  tccactggtctttccattgaattgtatccccaaacctgacaacattcgcacccgcacggtc
         A  I  L  T  A  P  G  T  N  T  E  E  A  K  A  M  Y  D  Y  L
2221  gctattctgacagctccaggtaccaataccgaagaagctaaggccatgtatgactatctt
         A  S  E  G  A  Y  V  D  Y  V  G  V  N  L  G  D  Q  G  G  L
2281  gcttcggaaggtgcctacgttgactatgtcggtgttaacctcggtgatcaaggcggtctg
         N  I  T  A  T  Y  L  H  T  S  S  V  L  Y  D  A  L  Y  V  P
2341  aacattactgctacgtatctgcatacctcgtctgtccttttacgatgctctctacgtcccc
         G  G  E  K  G  I  K  V  L  S  D  N  V  S  E  F  P  Y  D  E
2401  ggcggtgaaaagggtatcaaggtcttgtcagacaatgtgagcgagttcccgtacgatgaa
         P  K  V  F  V  L  D  A  Y  R  H  G  K  P  I  A  A  S  S  E
2461  cccaaggtctttgttctcgatgcctatcgccacggaaagcctattgcagcttccagcgaa
         G  V  K  F  I  N  S  A  V  N  M  D  I  Q  D  K  D  G  V  V
2521  ggtgtcaagtttatcaactctgccgtcaatatggatatccaagacaaggacggtgtagtc
         T  G  S  A  G  S  D  L  Q  T  E  F  K  K  A  L  I  Q  Q  R
2581  actgggtccgctggcagcgacctccaaacagaattcaagaaagcgctcatccagcagcga
         F  W  S  R  L  P  L  D  R  D  *
2641  ttctggtcacgattgccgcttgatcgtgactaa
```

Fig. 3 continued

```
      M   R   A   V   Q   L   L   P   S   L   A   G   L   I   G   A   A   S   A   V
   1  atgcgcgcagtgcagcttctgcccagcctcgccggcctgattggcgctgcctctgccgtt
      G   C   P   Y   L   T   G   Q   L   D   A   R   D   V   H   N   P   H   E   F
  61  ggatgtccgtatctgacgggccagctcgatgccagagacgtgcacaatccgcacgagttc
      Q   R   R   Q   D   P   G   D   A   A   A   S   T   E   Q   F   L   S   Q   F
 121  cagcgtcgacaggatcccggagatgcggctgcgtccacagagcagttcctgtcccagttc
      Y   L   N   D   S   N   S   Y   M   T   T   D   V   G   G   P   I   S   D   Q
 181  tatctcaatgacagcaacagctacatgaccactgatgtcggcggccccatctcggatcag
      N   S   L   K   A   G   E   R   G   P   T   L   L   E   D   F   I   F   R   Q
 241  aacagtttgaaggccggagagcgcggtccaaccctgttggaggacttcatcttccgtcag
      K   I   Q   H   F   D   H   E   R
 301  aagatccagcactttgatcacgagcggGTAGGTTGTACCATCCATGCGAGAGAGATCGAT
                                 V   P   E   R   A   V   H   A   R   G   A   G   A
 361  CGATGTTGACGTGGTGGCAGgtcccagaacgcgcagtccatgctcgaggagccggcgccc
      H   G   T   F   T   S   Y   G   N   W   S   N   I   T   A   A   S   F   L   S
 421  acggaacgttcacttcctacggaaactggtccaacatcactgcggcctccttcctgagcg
      A   E   G   K   E   T   P   V   F   V   R   F   S   T   V   A   G   S   R   G
 481  ctgaagggaaggagaccccgtgtttgtgcgcttctccaccgtggccggaagtcgaggca
      S   A   D   T   A   R   D   V   H   G   F   A   T   R   F   Y   T   D   E   G
 541  gtgcggacacggcgcgcgatgtgcatggctttgccaccaggttctacactgacgagggca
      N   F                                                           D   I
 601  actttgGTACGTCGTCTCACAATCCTCTCGACTGGCATCGTCTGACCGCTGAGCAGatat
      V   G   N   N   I   P   V   F   F   I   Q   D   A   I   L   F   P   D   L   I
 661  cgtcggcaacaacattccagtcttcttcatccaggacgccattctcttccctgatctgat
      H   A   V   K   P   S   P   D   N   E   I   P   Q   A   A   T   A   H   D   T
 721  ccatgctgtcaagcccagccccgacaacgagatcccccaggctgcgactgctcatgacac
      A   W   D   F   F   S   Q   Q   P   S   A   L   H   T   L   F   W   A   M   S
 781  ggcctgggacttcttcagccagcagcccagtgcgttgcacacgctcttctgggctatgtc
      G   H   G   I   P   R   S   F   R   H   M   D   G   F   V   H   T   F   R
 841  cggccatggaatccctcgctcttttcgccacatggacggctttggcgtccacactttccg
      F   V   T   D   D   G   A   S   K   L   V   K   F   H   W   T   S   L   Q   G
 901  attcgtgactgacgacggcgcctccaagctggtcaaattccactggacctcgctgcaggg
      R   A   S   L   V   W   E   E   A   Q   A   A   A   G   K   N   L   D   Y   M
 961  ccgggccagcctggtctgggaggaggcgcaagcggcagcgggaaagaacctggactatat
      R   Q   D   L   Y   D   N   I   E   A   G   R   Y   P   E   W   E
1021  gcgccaggacctctatgacaacatcgaagccggtcgatatcctgaatgggagGTAGGTGG
                                                                    L   G   I   Q   I   V
1081  CCGCATTTTCTCGGCATATATATGTCCATGCTGACGTTCCTAGctgggcattcaaatcgt
      D   E   E   D   Q   L   K   F   G   F   D   L   L   D   P   T   K   I   I   P
1141  cgacgaggaggatcagctcaagtttggatttgatctgctggatccaaccaagatcattcc
      V   E   Y   V   P   I   T   P   L   G   K   L   Q   L   N   R   N   P   L   N
1201  tgttgaatatgtccccatcacgccgcttgggaagctgcagctcaaccggaatccgctcaa
      Y   F   A   E   T   E   Q   I   M
1261  ctatttcgccgagacggagcagataatgGTATGTAAACAGTTTGTTGTTCGATTCTTTGC
                                    F   Q   P   G   H   I   V   R   G   I   D   F   T
1321  AGTAGACTGACGATACATAGttccaacccggccatattgtgcgcggaattgactttaccg
      E   D   P   L   L   Q   G   R   L   F   S   Y   L   D   T   Q   L   N   R   N
1381  aagaccccttctccagggacggctcttctcctatctcgacacgcagttgaatcggaatg
      G   G   P   N   F   E   Q   L   P   I   N   R   P   R   V   P   W   H   N   N
1441  gaggccccaatttcgagcagcttcccatcaatcgtcctagggtgccatggcataacaaca
      N   R   D   G   F
1501  accgtgatggattcaGTAAGTTTACCCCCCTGCGCTGACTCTCTGCATGCTAACTCCACC
                     S   Q   A   F   I   P   L   N   K   A   A   Y   S   P   N   T   L   N   N   G
1561  AGgccaagcgtttatccccctgaacaaggcggcctacagcccgaacacgctcaacaatgg
      N   P   K   Q   A   N   Q   T   V   G   D   G   F   F   T   T   P   G   R   T
1621  caaccccaagcaggcgaaccagactgtgggcgatggattcttcaccactcccggacgtac
      T   S   G   R   L   M   R   T   V   S   S   T   F   S   D   V   W   S   Q   P
1681  gaccagtggccggctcatgcgcaccgtcagttcgaccttctccgacgtctggtcgcagcc
```

Fig. 4

```
           R   L   F   Y   N   S   L   V   P   A   E   Q   Q   F   L   V   N   A   I   R
1741   tcggctgttctacaactcgctggtgccggccgagcagcagttcctcgtcaacgccatccg
           F   E   N   S   N   V   K   S   E   V   V   R   N   N   V   I   I   Q   L   N
1801   tttcgagaactccaacgtcaagagcgaagtggtccggaacaatgtcatcatccagctcaa
           R   V   D   N   D   L   A   R   R   V   A   R   V   I   G   V   A   E   P   E
1861   ccgcgtcgataacgacctcgcccgccgggttgctcgggtcattggcgttgcagaacccga
           P   D   P   T   Y   Y   H   N   N   K   T   A   N   V   G   T   F   G   T   P
1921   gcccgatccaacctattatcacaacaacaagacggccaacgtgggtacgtttggcacgcc
           L   K   R   I   D   G   L   K   V   G   V   L   A   T   V   G   D   P   D   S
1981   gctcaagcggatcgacggtctcaaagtcggtgtgcttgccacagttggcgacccagacag
           I   S   Q   G   Q   S   L   S   D   A   L   S   D   S   K   V   D   V   T   V
2041   tatcagtcagggccagagcctcagtgacgcgctctcggactccaaggtcgatgtcactgt
           V   A   E   S   F   T   D   G   V   D   A   L   Y   T   N   S   D   A   T   G
2101   cgttgctgagtctttcacggacggggtcgatgcgctctacaccaactcggacgcgaccgg
           F   D   A   V   I   V   A   D   G   A   E   G   L   F   T   P   S   S   F   T
2161   cttcgacgccgttatcgtggctgatggcgccgaagggcttttttaccccgagtagcttcac
           A   K   P   T   N   S   F   S   T   T   T   L   Y   P   A   G   R   P   L   Q
2221   agccaaaccgacgaactcattctcgacgacaacgctttatccggccggtcgtccgctgca
           I   L   V   D   A   F   R   F   G   K   P   V   G   A   L   G   S   G   A   K
2281   gatcctggtcgacgccttccggttcggcaagcccgtcggcgctctgggcagcggagctaa
           A   L   D   A   A   G   I   S   T   S   R   P   G   V   Y   V   A   N   S   T
2341   ggcgcttgatgcggcaggtatctcgactagccggcctggtgtgtacgtcgccaactcgac
           S   E   A   F   T   D   D   I   E   D   G   L   R   T   F   K   F   L   D   R
2401   cagcgaggcgttcacggacgatatcgaggatggtttgcgaacgttcaagttcctcgaccg
           F   A   L   D   E   *
2461   gtttgcgctggatgagtga
```

POLYPEPTIDES HAVING CATALASE ACTIVITY AND POLYNUCLEOTIDES ENCODING SAME

CROSS-REFERENCE TO RELATED APPLICATIONS

This application is a 35 U.S.C. 371 national application of PCT/CN2012/086946 filed Dec. 19, 2012 which claims priority or the benefit under 35 U.S.C. 119 of Chinese PCT application no. PCT/CN2011/084230 filed Dec. 19, 2011 and U.S. provisional application No. 61/582,913 filed Jan. 4, 2012, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having catalase activity and catalytic domains, and polynucleotides encoding the polypeptides, and catalytic domains. The invention also relates to nucleic acid constructs, vectors, and host cells comprising the polynucleotides as well as methods of producing and using the polypeptides, and catalytic domains.

Description of the Related Art

Catalases [hydrogen peroxide:hydrogen peroxide oxidoreductases (EC 1.11.1.6)] are enzymes which catalyze the conversion of hydrogen peroxide ($H_2O_2$) to oxygen ($O_2$) and water ($H_2O$). These ubiquitous enzymes have been purified from a variety of animal tissues, plants and microorganisms (Chance and Maehly, 1955, *Methods Enzymol.* 2: 764-791).

Catalase preparations are used commercially for diagnostic enzyme kits, for the enzymatic production of sodium gluconate from glucose, for the neutralization of $H_2O_2$ waste, and for the removal of $H_2O_2$ and/or generation of $O_2$ in foods and beverages.

WO 92/17571 discloses a catalase, which retain activity at higher temperature and pH than other known catalases, from strains of *Scytalidium* and *Humicola*. UNIPROT:AIDJU9 discloses a deduced amino acid sequence of catalase from *Neosartorya fischeri*. UNIPROT:P30266 discloses a catalase from *Bacillus pseudofirmu*. UNIPROT:P42234 discloses a catalase polypeptide from *Bacillus subtilis*. JP2007143405-A discloses a catalase from *Thermoascus aurantiacus*.

The present invention provides polypeptides having catalase activity and polynucleotides encoding the polypeptides.

SUMMARY OF THE INVENTION

The present invention relates to isolated polypeptides having catalase activity selected from the group consisting of:

(a) a polypeptide having at least 83% sequence identity to the mature polypeptide of SEQ ID NO: 8, at least at least 76% sequence identity to the mature polypeptide of SEQ ID NO: 2, at least 60% sequence identity to the mature polypeptide of SEQ ID NO: 4, or at least 60% sequence identity to the mature polypeptide of SEQ ID NO: 6;

(b) a polypeptide encoded by a polynucleotide that hybridizes under low, medium, medium-high, high, or very high stringency conditions with (i) the mature polypeptide coding sequence of SEQ ID NO: 7, the mature polypeptide coding sequence of SEQ ID NO: 1, the mature polypeptide coding sequence of SEQ ID NO: 3, or the mature polypeptide coding sequence of SEQ ID NO: 5, (ii) the cDNA sequence thereof, or (iii) the full-length complement of (i) or (ii);

(c) a polypeptide encoded by a polynucleotide having at least 83% sequence identity to the mature polypeptide coding sequence of SEQ ID NO: 7, at least 76% sequence identity to the mature polypeptide coding sequence of SEQ ID NO: 1, at least 60% sequence identity to the mature polypeptide coding sequence of SEQ ID NO: 3, or at least 60% sequence identity to the mature polypeptide coding sequence of SEQ ID NO: 5; or the cDNA sequence thereof;

(d) a variant of the mature polypeptide of SEQ ID NO: 8, a variant of the mature polypeptide of SEQ ID NO: 2, a variant of the mature polypeptide of SEQ ID NO: 4, or a variant of the mature polypeptide of SEQ ID NO: 6, comprising a substitution, deletion, and/or insertion at one or more (e.g., several) positions; and (e) a fragment of the polypeptide of (a), (b), (c), or (d) that has catalase activity.

The present invention also relates to isolated polypeptides comprising a catalytic domain selected from the group consisting of:

(a) a catalytic domain having at least 83% sequence identity to amino acids 20 to 740 of SEQ ID NO: 8, a catalytic domain having at least 76% sequence identity to amino acids 17 to 723 of SEQ ID NO: 2, a catalytic domain having at least 60% sequence identity to amino acids 38 to 723 of SEQ ID NO: 4, or a catalytic domain having at least 60% sequence identity to amino acids 38 to 711 of SEQ ID NO: 6;

(b) a polypeptide encoded by a polynucleotide that hybridizes under low, medium, medium-high, high, or very high stringency conditions with (i) nucleotides 58 to 2473 of SEQ ID NO: 7, nucleotides 49 to 2601 of SEQ ID NO: 1, nucleotides 112 to 2687 of SEQ ID NO: 3, or nucleotides 112 to 2652 of SEQ ID NO: 5, (ii) the cDNA sequence thereof, or (iii) the full-length complement of (i) or (ii);

(c) a catalytic domain encoded by a polynucleotide having at least 83% sequence identity to nucleotides 58 to 2473 of SEQ ID NO: 7, a catalytic domain encoded by a polynucleotide having at least 76% sequence identity to nucleotides 49 to 2601 of SEQ ID NO: 1, a catalytic domain encoded by a polynucleotide having at least 60% sequence identity to nucleotides 112 to 2687 of SEQ ID NO: 3, or a catalytic domain encoded by a polynucleotide having at least 60% sequence identity to nucleotides 112 to 2652 of SEQ ID NO: 5;

(d) a variant of amino acids 20 to 740 of SEQ ID NO: 8, a variant of amino acids 17 to 723 of SEQ ID NO: 2, a variant of amino acids 38 to 723 of SEQ ID NO: 4, or a variant of amino acids 38 to 711 of SEQ ID NO: 6, comprising a substitution, deletion, and/or insertion at one or more (e.g., several) positions; and (e) a fragment of the catalytic domain of (a), (b), (c), or (d) which has catalase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to processes for degrading or converting a cellulosic material, comprising: treating the cellulosic material with an enzyme composition in the presence of a polypeptide having catalase activity of the present invention. In one aspect, the processes further comprise recovering the degraded or converted cellulosic material.

The present invention also relates to processes of producing a fermentation product, comprising: (a) saccharifying a cellulosic material with an enzyme composition in the presence of a polypeptide having catalase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having catalase activity of the present invention. In one aspect, the fermenting of the cellulosic material produces a fermentation product. In another aspect, the processes further comprise recovering the fermentation product from the fermentation.

The present invention also relates to a polynucleotide encoding a signal peptide comprising or consisting of amino acids 1 to 19 of SEQ ID NO: 8, amino acids 1 to 16 of SEQ ID NO: 2, amino acids 1 to 20 of SEQ ID NO: 4, or amino acids 1 to 24 of SEQ ID NO: 6, which is operably linked to a gene encoding a protein; nucleic acid constructs, expression vectors, and recombinant host cells comprising the polynucleotides; and methods of producing a protein.

BRIEF DESCRIPTION OF THE FIGURES

FIG. 1 shows the genomic DNA sequence (SEQ ID NO: 1) and the deduced amino acid sequence (SEQ ID NO: 2) of a *Malbranchea cinnamomea* catalase gene.

FIG. 2 shows the genomic DNA sequence (SEQ ID NO: 3) and the deduced amino acid sequence (SEQ ID NO: 4) of a *Rhizomucor pusillus* catalase gene.

FIG. 3 shows the genomic DNA sequence (SEQ ID NO: 5) and the deduced amino acid sequence (SEQ ID NO: 6) of a *Rhizomucor pusillus* catalase gene.

FIG. 4 shows the genomic DNA sequence (SEQ ID NO: 7) and the deduced amino acid sequence (SEQ ID NO: 8) of a *Penicillium emersonii* catalase gene.

DEFINITIONS

Figure 5:
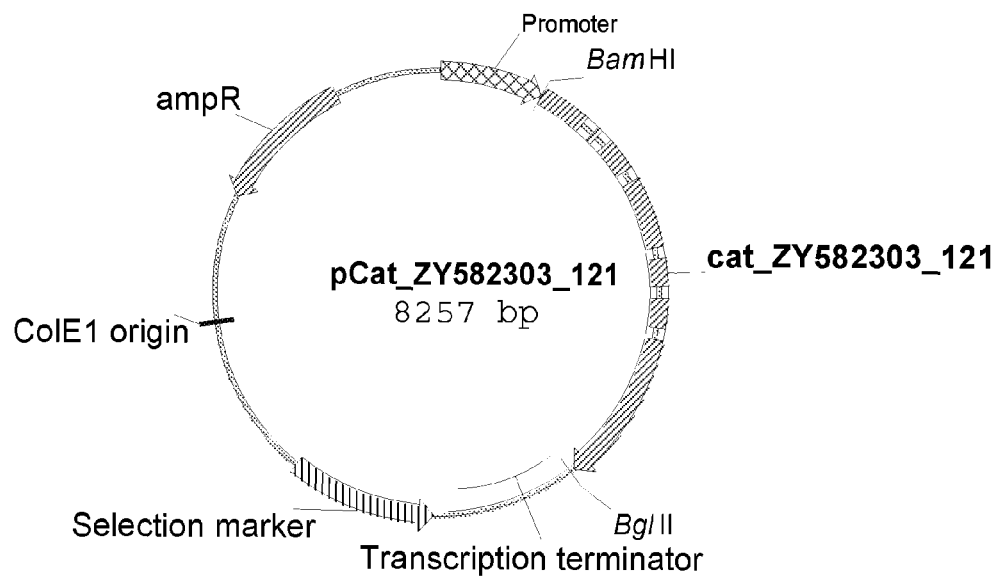
FIG. 5 shows a restriction map of pCat_ZY582303_121.

Catalase: The term "catalase activity" is defined herein as a hydrogen-peroxide:hydrogen-peroxide oxidoreductase activity (EC 1.11.1.6) that catalyzes the conversion of $2H_2O_2$ to $O_2+2 H_2O$. For purposes of the present invention, catalase activity is determined according to U.S. Pat. No. 5,646,025. One unit of catalase activity equals the amount of enzyme that catalyzes the oxidation of 1 µmole of hydrogen peroxide under the assay conditions. Alternatively, the catalase activity can be determined using the procedure described in Examples 17 and 18 of the present invention.

In one aspect, the polypeptides of the present invention have at least 20%, e.g., at least 40%, at least 50%, at least 60%, at least 70%, at least 80%, at least 90%, at least 95%, or at least 100% of the catalase activity of the mature polypeptide of SEQ ID NO: 2, the mature polypeptide of SEQ ID NO: 4, the mature polypeptide of SEQ ID NO: 6, or the mature polypeptide of SEQ ID NO: 8.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, J. Bacteriol. 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermo-*

*philum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No1 filter paper, microcrystalline cellulose, bacterial cellulose, algal cellulose, cotton, pretreated lignocellulose, etc. The most common total cellulolytic activity assay is the filter paper assay using Whatman No1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Wash. D.C.; Wyman, 1994, *Bioresource Technology* 50: 3-16; Lynd, 1990, *Applied Biochemistry and Biotechnology* 24/25: 695-719; Mosier et al, 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No1 filter paper, microcrystalline cellulose, bacterial cellulose, algal cellulose, cotton, pretreated lignocellulose, etc. The most common total cellulolytic activity assay is the filter paper assay using Whatman No1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Fragment: The term "fragment" means a polypeptide having one or more (e.g., several) amino acids absent from the amino and/or carboxyl terminus of a mature polypeptide main; wherein the fragment has catalase activity. In another aspect, a fragment contains at least 614 amino acid residues, e.g., at least 650 amino acid residues or at least 686 amino acid residues of SEQ ID NO: 8. In one aspect, a fragment contains at least 604 amino acid residues, e.g., at least 640 amino acid residues or at least 676 amino acid residues of SEQ ID NO: 2. In another aspect, a fragment contains at least 602 amino acid residues, e.g., at least 638 amino acid residues or at least 674 amino acid residues of SEQ ID NO: 4. In another aspect, a fragment contains at least 588 amino acid residues, e.g., at least 623 amino acid residues or at least 658 amino acid residues of SEQ ID NO: 6.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance)

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In another aspect, the mature polypeptide is amino acids 20 to 741 of SEQ ID NO: 8 based on the SignalP program that predicts amino acids 1 to 19 of SEQ ID NO: 8 are a signal peptide. In one aspect, the mature polypeptide is amino acids 17 to 729 of SEQ ID NO: 2 based on the SignalP program (Nielsen et al., 1997, *Protein Engineering* 10: 1-6) that predicts amino acids 1 to 16 of SEQ ID NO: 2 are a signal peptide. In another aspect, the mature polypeptide is amino acids 21 to 730 of SEQ ID NO: 4 based on the SignalP program that predicts amino acids 1 to 20 of SEQ ID NO: 4 are a signal peptide. In another aspect, the mature polypeptide is amino acids 25 to 717 of SEQ ID NO: 6 based on the SignalP program that predicts amino acids 1 to 24 of SEQ ID NO: 6 are a signal peptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having catalase activity. In another aspect, the mature polypeptide coding sequence is nucleotides 58 to 2476 of SEQ ID NO: 7 or the cDNA sequence thereof based on the SignalP program that predicts nucleotides 1 to 57 of SEQ ID NO: 7 encode a signal peptide. In one aspect, the mature polypeptide coding sequence is nucleotides 49 to 2619 of SEQ ID NO: 1 or the cDNA sequence thereof based on the SignalP program (Nielsen et al., 1997, supra) that predicts nucleotides 1 to 48 of SEQ ID NO: 1 encode a signal peptide. In another aspect, the mature polypeptide coding sequence is nucleotides 61 to 2708 of SEQ ID NO: 3 or the cDNA sequence thereof based on the SignalP program that predicts nucleotides 1 to 60 of SEQ ID NO: 3 encode a signal peptide. In another aspect, the mature polypeptide coding sequence is nucleotides 73 to 2670 of SEQ ID NO: 5 or the cDNA sequence thereof based on the SignalP program that predicts nucleotides 1 to 72 of SEQ ID NO: 5 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and a suitable pH such 4-9, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0, 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having catalase activity. In another aspect, a subsequence contains at least 1842 nucleotides, e.g., at least 1950 nucleotides or at least 2058 nucleotides of SEQ ID NO: 7. In one aspect, a subsequence contains at least 1812 nucleotides, e.g., at least 1920 nucleotides or at least 2028 nucleotides of SEQ ID NO: 1. In another aspect, a subsequence contains at least 1806 nucleotides, e.g., at least 1914 nucleotides or at least 2022 nucleotides of SEQ ID NO: 3. In another aspect, a subsequence contains at least 1764 nucleotides, e.g., at least 1869 nucleotides or at least 1974 nucleotides of SEQ ID NO: 5.

Variant: The term "variant" means a polypeptide having catalase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, Recent progress in the assays of xylanolytic enzymes, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Catalase Activity

In an embodiment, the present invention relates to isolated polypeptides having a sequence identity to the mature polypeptide of SEQ ID NO: 8 of at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have catalase activity. In an embodiment, the present invention relates to isolated polypeptides having a sequence identity to the mature polypeptide of SEQ ID NO: 2 of at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have catalase activity. In an embodiment, the present invention relates to isolated polypeptides having a sequence identity to the mature polypeptide of SEQ ID NO: 4 of at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have catalase activity. In an embodiment, the present invention relates to isolated polypeptides having a sequence identity to the mature polypeptide of SEQ ID NO: 6 of at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have catalase activity. In one aspect, the polypeptides differ by up to 10 amino acids, e.g., 1, 2, 3, 4, 5, 6, 7, 8, 9 or 10, from the mature polypeptide of SEQ ID NO: 8, the mature polypeptide of SEQ ID NO: 2, the mature polypeptide of SEQ ID NO: 4, or the mature polypeptide of SEQ ID NO: 6.

A polypeptide of the present invention preferably comprises or consists of the amino acid sequence of SEQ ID NO: 8, SEQ ID NO: 2, SEQ ID NO: 4, or SEQ ID NO: 6 or an allelic variant thereof; or is a fragment thereof having catalase activity. In another aspect, the polypeptide comprises or consists of the mature polypeptide of SEQ ID NO: 8, the mature polypeptide of SEQ ID NO: 2, the mature polypeptide of SEQ ID NO: 4, or the mature polypeptide of SEQ ID NO: 6. In another aspect, the polypeptide comprises or consists of amino acids 20 to 741 of SEQ ID NO: 8, amino acids 17 to 729 of SEQ ID NO: 2, amino acids 21 to 730 of SEQ ID NO: 4, or amino acids 25 to 717 of SEQ ID NO: 6.

In another embodiment, the present invention relates to an isolated polypeptide having catalase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 7, the mature polypeptide coding sequence of SEQ ID NO: 1, the mature polypeptide coding sequence of SEQ ID NO: 3, or the mature polypeptide coding sequence of SEQ ID NO: 5, (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO: 7, SEQ ID NO: 1, SEQ ID NO: 3, or SEQ ID NO: 5, or a subsequence thereof, as well as the polypeptide of SEQ ID NO: 8, SEQ ID NO: 2, SEQ ID NO: 4, or SEQ ID NO: 6, or a fragment thereof, may be used to design nucleic acid probes to identify and clone DNA encoding polypeptides having catalase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having catalase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 7, SEQ ID NO: 1, SEQ ID NO: 3, or SEQ ID NO: 5, or the mature polypeptide coding sequence thereof, or a subsequence thereof, the carrier material is used in a Southern blot.

For purposes of the present invention, hybridization indicates that the polynucleotides hybridize to a labeled nucleic acid probe corresponding to (i) SEQ ID NO: 7, SEQ ID NO: 1, SEQ ID NO: 3, or SEQ ID NO: 5; (ii) the mature polypeptide coding sequence of SEQ ID NO: 7, the mature polypeptide coding sequence of SEQ ID NO: 1, the mature polypeptide coding sequence of SEQ ID NO: 3, or the mature polypeptide coding sequence of SEQ ID NO: 5; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 8, SEQ ID NO: 2, SEQ ID NO: 4, or SEQ ID NO: 6, or the mature polypeptide thereof; or a fragment thereof. In another aspect, the nucleic acid probe is SEQ ID NO: 7, SEQ ID NO: 1, SEQ ID NO: 3, or SEQ ID NO: 5; or the cDNA sequence thereof. In one aspect, the nucleic acid probe is the mature polypeptide coding sequence of SEQ ID NO: 7, the mature polypeptide coding sequence of SEQ ID NO: 1, the mature polypeptide coding sequence of SEQ ID NO: 3, or the mature polypeptide coding sequence of SEQ ID NO: 5.

In another embodiment, the present invention relates to isolated polypeptides having catalase activity encoded by a polynucleotide having a sequence identity to the mature polypeptide coding sequence of SEQ ID NO: 7, or the cDNA sequence thereof, of at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In another embodiment, the present invention relates to isolated polypeptides having catalase activity encoded by a polynucleotide having a sequence identity to the mature polypeptide coding sequence of SEQ ID NO: 1, or the cDNA sequence thereof, of at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having catalase activity encoded by a polynucleotide having a sequence identity to the mature polypeptide coding sequence of SEQ ID NO: 3, or the cDNA sequence thereof, of at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having catalase activity encoded by a polynucleotide having a sequence identity to the mature polypeptide coding sequence of SEQ ID NO: 5, or the cDNA sequence thereof, of at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 8, variants of the mature polypeptide of SEQ ID NO: 2, variants of the mature polypeptide of SEQ ID NO: 4, or variants of the mature polypeptide of SEQ ID NO: 6, comprising a substitution, deletion, and/or insertion at one or more (e.g., several) positions. In an embodiment, the number of amino acid substitutions, deletions and/or insertions introduced into the mature polypeptide of SEQ ID NO: 8, the mature polypeptide of SEQ ID NO: 2, the mature polypeptide of SEQ ID NO: 4, or the mature polypeptide of SEQ ID NO: 6, is up to 10, e.g., 1, 2, 3, 4, 5, 6, 7, 8, 9 or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for catalase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol* 3: 568-576; Svetina et al, 2000, *J. Biotechnol* 76: 245-251; Rasmussen-Wilson et al, 1997, *Appl. Environ. Microbiol* 63: 3488-3493; Ward et al, 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Catalase Activity

A polypeptide having catalase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly. The polypeptide may be a fungal polypeptide. For example, the polypeptide may be a *Malbranchea*, *Penicillium*, or *Rhizomucor*, polypeptide.

In another aspect, the polypeptide is a *Malbranchea cinnamomea* polypeptide. In another aspect, the polypeptide is a *Rhizomucor pusillus* polypeptide. In another aspect, the polypeptide is a *Penicillium emersonii* polypeptide. In another aspect, the polypeptide is a *Penicillium funiculosum* polypeptide. In another aspect, the polypeptide is a *Penicillium purpurogenum* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention relates to catalytic domains having a sequence identity to amino acids 20 to 740 of SEQ ID NO: 8 of at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one embodiment, the present invention relates to catalytic domains having a sequence identity to amino acids 17 to 723 of SEQ ID NO: 2 of at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one embodiment, the present invention relates to catalytic domains having a sequence identity to amino acids 38 to 723 of SEQ ID NO: 4 of at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one embodiment, the present invention relates to catalytic domains having a sequence identity to amino acids 38 to 711 of SEQ ID NO: 6 of at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 20 to 740 of SEQ ID NO: 8, amino acids 17 to 723 of SEQ ID NO: 2, amino acids 38 to 723 of SEQ ID NO: 4, or amino acids 38 to 711 of SEQ ID NO: 6.

The catalytic domain preferably comprises or consists of amino acids 20 to 740 of SEQ ID NO: 8 or an allelic variant thereof; or is a fragment thereof having catalase activity. The catalytic domain preferably comprises or consists of amino acids 17 to 723 of SEQ ID NO: 2 or an allelic variant thereof; or is a fragment thereof having catalase activity. The catalytic domain preferably comprises or consists of amino acids 38 to 723 of SEQ ID NO: 4 or an allelic variant thereof; or is a fragment thereof having catalase activity. The catalytic domain preferably comprises or consists of amino acids 38 to 711 of SEQ ID NO: 6 or an allelic variant thereof; or is a fragment thereof having catalase activity.

In another embodiment, the present invention relates to catalytic domains encoded by polynucleotides that hybridize under very low stringency conditions, low stringency conditions, medium stringency conditions, medium-high stringency conditions, high stringency conditions, and very high stringency conditions (as defined above) with nucleotides 58 to 2473 of SEQ ID NO: 7, nucleotides 49 to 2601 of SEQ ID NO: 1, nucleotides 112 to 2687 of SEQ ID NO: 3, or nucleotides 112 to 2652 of SEQ ID NO: 5, or the full-length complement thereof (Sambrook et al., 1989, supra).

In another embodiment, the present invention relates to catalytic domains encoded by polynucleotides having a sequence identity to nucleotides 58 to 2473 of SEQ ID NO: 7 of at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In another embodiment, the present invention relates to catalytic domains encoded by polynucleotides having a sequence identity to nucleotides 49 to 2601 of SEQ ID NO: 1 of at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In another embodiment, the present invention relates to catalytic domains encoded by polynucleotides having a sequence identity to nucleotides 112 to 2687 of SEQ ID NO: 3 of at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In another embodiment, the present invention relates to catalytic domains encoded by polynucleotides having a sequence identity to nucleotides 112 to 2652 of SEQ ID NO: 5 of at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The polynucleotide encoding the catalytic domain preferably comprises or consists of nucleotides 58 to 2473 of SEQ ID NO: 7. The polynucleotide encoding the catalytic domain preferably comprises or consists of nucleotides 49 to 2601 of SEQ ID NO: 1. The polynucleotide encoding the catalytic domain preferably comprises or consists of nucleotides 112 to 2687 of SEQ ID NO: 3. The polynucleotide encoding the catalytic domain preferably comprises or consists of nucleotides 112 to 2652 of SEQ ID NO: 5.

In another embodiment, the present invention relates to catalytic domain variants of amino acids 20 to 740 of SEQ ID NO: 8, catalytic domain variants of amino acids 17 to 723 of SEQ ID NO: 2, catalytic domain variants of amino acids 38 to 723 of SEQ ID NO: 4 or catalytic domain variants of amino acids 38 to 711 of SEQ ID NO: 6, comprising a substitution, deletion, and/or insertion at one or more (e.g., several) positions. In one aspect, the number of amino acid substitutions, deletions and/or insertions introduced into the sequence of amino acids 20 to 740 of SEQ ID NO: 8, amino acids 17 to 723 of SEQ ID NO: 2, amino acids 38 to 723 of SEQ ID NO: 4, or amino acids 38 to 711 of SEQ ID NO: 6, is up to 10, e.g., 1, 2, 3, 4, 5, 6, 8, 9, or 10.

Polynucleotides

The present invention also relates to isolated polynucleotides encoding a polypeptide, a catalytic domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al, 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Malbranchea, Rhizomucor* or *Penicillium*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 7, the mature polypeptide coding sequence of SEQ ID NO: 1, the mature polypeptide coding sequence of SEQ ID NO: 3, or the mature polypeptide coding sequence of SEQ ID NO: 5, or the cDNA sequence thereof, or a subsequence thereof, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al, 1991, *Protein Expression and Purification* 2: 95-107.

Nucleic Acid Constructs

The present invention also relates to nucleic acid constructs comprising a polynucleotide of the present invention operably linked to one or more control (e.g., several) sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al, 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al, 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus otyzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (e.g., several) convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ111 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al, 1991, *Gene* 98: 61-67; Cullen et al, 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al, 1989, supra).

Host Cells

The present invention also relates to recombinant host cells, comprising a polynucleotide of the present invention operably linked to one or more (e.g., several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al, 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol (Praha)* 49: 399-405), conjugation (see, e.g., Mazodier et al, 1989, *J. Bacteriol.* 171: 3583-3585), or transduction (see, e.g., Burke et al, 2001, *Proc. Natl. Acad. Sci. USA* 98: 6289-6294). The introduction of DNA into a *Pseudomonas* cell may be effected by electroporation (see, e.g., Choi et al, 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium*

*bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus etyngii, Thielavia terrestris, Trametes villosa, Trametes versicolor, Trichoderma hatzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally (b) recovering the polypeptide. In a preferred aspect, the cell is a *Malbranchea* cell. In a more preferred aspect, the cell is a *Malbranchea cinnamomea* cell. In a most preferred aspect, the cell is *Malbranchea cinnamomea* NN044758. In a preferred aspect, the cell is a *Rhizomucor* cell. In a more preferred aspect, the cell is a *Rhizomucor pusillus* cell. In a most preferred aspect, the cell is *Rhizomucor pusillus* NN046782. In another aspect, the cell is a *Penicillium* cell. In another aspect, the cell is a *Penicillium emersonii* cell. In another aspect, the cell is a *Penicillium emersonii* NNO51602.

The present invention also relates to methods of producing a polypeptide of the present invention, comprising (a) cultivating a recombinant host cell of the present invention under conditions conducive for production of the polypeptide; and optionally (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell PhysioL* 39: 885-889), a *Vicia faba* promoter from the legumin B4 and the unknown seed protein gene from *Vicia faba* (Conrad et al, 1998, *J. Plant Physiol* 152: 708-711), a promoter from a seed oil body protein (Chen et al., 1998, *Plant Cell Physiol* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al, 1993, *Plant Physiol* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al, 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al, 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al, 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and optionally (b) recovering the polypeptide or domain.

Removal or Reduction of Catalase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having catalase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 7, the mature polypeptide coding sequence of SEQ ID NO: 1, the mature polypeptide coding sequence of SEQ ID NO: 3, or the mature polypeptide coding sequence of SEQ ID NO: 5, for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and optionally (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially catalase-free product are of particular interest in the production of eukaryotic polypeptides, in particular fungal proteins such as enzymes. The catalase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from catalase activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the catalase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

In general terms, the polypeptide can be used in any situation in which it is desired to remove residual hydrogen peroxide from a mixture to which hydrogen peroxide has been added or generated, e.g., for pasteurization or bleaching.

The polypeptides having catalase activity of the present invention can be used commercially for diagnostic enzyme kits, for the enzymatic production of sodium gluconate from glucose, for the neutralization of $H_2O_2$ waste, and for the removal of $H_2O_2$ and/or generation of $O_2$ in foods and beverages using methods well established in the art.

In one aspect, the present invention also relates to methods for removing hydrogen peroxide, comprising treating a mixture to which hydrogen peroxide has been added or generated with a polypeptide of the present invention.

In one aspect, the present invention relates to a method for removing hydrogen peroxide from textile.

During textile manufacturing, hydrogen peroxide is used in the bleaching step to completely remove colored impurities, improve absorbency, and achieve adequate whiteness and dyeability. However, excess peroxide product remains on the textile and it can interfere with and have an adverse affect on subsequent dyeings with anionic dyes, for example, reactive dyes where the dye is in part or totally destroyed. Genenrally, catalase is applied after the bleaching step to help to destroy excess hydrogen peroxide. In another aspect, the present invention also relates to methods for generating molecular oxygen, comprising treating a mixture to which hydrogen peroxide has been added or generated with a polypeptide of the present invention.

The present invention is also directed to the following processes for using the polypeptides having catalase activity, or compositions thereof.

The present invention also relates to processes for degrading or converting a cellulosic material, comprising: treating the cellulosic material with an enzyme composition in the presence of a polypeptide having catalase activity of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having catalase activity of the present invention; (b) fermenting the saccharified cellulosic material with one or more (e.g., several) fermenting microorganisms to produce the fermentation product; and (c) recovering the fermentation product from the fermentation. The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having catalase activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment. In practicing the processes of the present invention, any pretreatment process known in the art can be used to disrupt plant cell wall components of the cellulosic material (Chandra et al, 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al, 2006, *Appl. Biochem. Biotechnol.* 129-132: 496-508; Varga et al., 2004, *Appl. Biochem. Biotechnol.* 113-116: 509-523; Sassner et al, 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al, 2004, *Bioresource Technol.* 91: 179-188; Lee et al, 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al, 2005, *Bioresource Technol* 96: 1959-1966; Mosier et al., 2005, *Bioresource Technol* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol* 64: 139-151; Palonen et al, 2004, *Appl. Biochem. Biotechnol.* 117: 1-17; Varga et al, 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having catalase activity of the present invention. The enzyme components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading or converting the cellulosic material.

In one aspect, the enzyme composition comprises or further comprises one or more (e.g., several) proteins/polypeptides selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endo-glucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulationor a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having catalase activity depend on several factors including, but not limited to, the mixture of cellulolytic and/or hemicellulolytic enzyme components, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having catalase activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having catalase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram-positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, *Caldicellulosiruptor*, *Acidothermus*, *Thermobifidia*, or *Oceanobacillus* polypeptide having enzyme activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having enzyme activity.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having enzyme activity.

In another aspect, the polypeptide is a *Streptococcus equisimilis*, *Streptococcus pyogenes*, *Streptococcus uberis*, or *Streptococcus equi* subsp. *Zooepidemicus* polypeptide having enzyme activity.

In another aspect, the polypeptide is a *Streptomyces achromogenes*, *Streptomyces avermitilis*, *Streptomyces coelicolor*, *Streptomyces griseus*, or *Streptomyces lividans* polypeptide having enzyme activity.

The polypeptide having enzyme activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having enzyme activity; or more preferably a filamentous fungal polypeptide such as an *Acremonium*, *Agaricus*, *Altemrnaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvatiella*, or *Xylaria* polypeptide having enzyme activity.

In one aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having enzyme activity.

In another aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdatium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, *Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM). ROHAMENT™ 7069 W (Röhm GmbH), FIBREZYME® LDI (Dyadic International, Inc.), FIBREZYME® LBR (Dyadic International, Inc.), or VISCOSTAR® 150 L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, Cladorrhinum foecundissimum ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al, 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum*

(WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese or copper.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl) furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740 L (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448). Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), More Gene Manipulations in Fungi, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation. The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is (are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al, 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, FEMS Yeast Research 4: 655-664; Beall et al, 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al, Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products: A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to isolated polynucleotides encoding a signal peptide comprising or consisting of amino acids 1 to 19 of SEQ ID NO: 8, amino acids 1 to 16 of SEQ ID NO: 2, amino acids 1 to 20 of SEQ ID NO: 4, or amino acids 1 to 24 of SEQ ID NO: 6. The polynucleotide may further comprise a gene encoding a protein, which is operably linked to the signal peptide. The protein is preferably foreign to the signal peptide. In another aspect, the polynucleotide encoding the signal peptide is nucleotides 1 to 57 of SEQ ID NO: 7. In one aspect, the polynucleotide encoding the signal peptide is nucleotides 1 to 48 of SEQ ID NO: 1. In another aspect, the polynucleotide encoding the signal peptide is nucleotides 1 to 60 of SEQ ID NO: 3. In another aspect, the polynucleotide encoding the signal peptide is nucleotides 1 to 72 of SEQ ID NO: 5.

The present invention also relates to nucleic acid constructs, expression vectors and recombinant host cells comprising such polynucleotides.

The present invention also relates to methods of producing a protein, comprising (a) cultivating a recombinant host cell comprising such a polynucleotide operably linked to a gene encoding the protein; and optionally (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strain

The fungal strain NN044758 was isolated from a soil sample collected from Yunnan Province in China by the dilution plate method with PDA medium at 45° C. It was then purified by transferring a single conidium onto a YG agar plate. The strain NN044758 was identified as *Malbranchea cinnamomea*, based on both morphological characteristics and ITS rDNA sequence.

The fungal strain NN046782 was isolated from a soil sample collected from Hunan Province in China. The strain NN046872 was identified as *Rhizomucor pusillus*, based on both morphological characteristics and ITS rDNA sequence.

The fungal strain NN051602 was isolated from a compost sample collected from Yunnan Province, China by the dilution plate method with PDA medium at 45° C. It was then purified by transferring a single conidium onto a YG agar plate. The strain NN051602 was identified as *Penicillium emersonii*, based on both morphological characteristics and ITS rDNA sequence.

Media

PDA medium was composed of 39 grams of potato dextrose agar and deionized water to 1 liter.

YG agar plate was composed of 5.0 g of yeast extract, 10.0 g of glucose, 20.0 g of agar, and deionized water to 1 liter.

YPG medium was composed of 0.4% of yeast extract, 0.1% of $KH_2PO_4$, 0.05% of $MgSO_4.7H_2O$, 1.5% glucose in deionized water.

YPM medium was composed of 1% yeast extract, 2% of peptone, and 2% of maltose in deionized water.

Minimal medium plates were composed of 342 g of sucrose, 20 ml of salt solution, 20 g of agar, and deionized water to 1 liter. The salt solution was composed of 2.6% KCl, 2.6% $MgSO_4.7H_2O$, 7.6% $KH_2PO_4$, 2 ppm $Na_2B_4O_7.10H_2O$, 20 ppm $CuSO_4.5H_2O$, 40 ppm $FeSO_4.7H_2O$, 40 ppm $MnSO_4.2H_2O$, 40 ppm $Na_2MoO_4.2H_2O$, and 400 ppm $ZnSO_4.7H_2O$.

FG4 medium was composed of 30 g of soymeal, 15 g of maltose, 5 g of peptone, and deionized water to 1 liter.

Example 1

*Malbranchea cinnamomea* Genomic DNA Extraction

*Malbranchea cinnamomea* strain NN044758 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen under liquid nitrogen. Frozen mycelia were ground, by a mortar and a pestle, to a fine powder, and genomic DNA was isolated using Large-Scale Column Fungal DNAout (BAOMAN BIOTECHNOLOGY, Shanghai, China) following the manufacturer's instruction.

Example 2

Genome Sequencing, Assembly and Annotation

The extracted genomic DNA samples were delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene identification and functional prediction. GeneID (Parra et al., 2000, *Genome Research* 10(4):511-515) was used for gene prediction. Blastall version 2.2.10 (Altschul et al., 1990, *J. Mol. Biol.* 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The catalase was identified by analysis of the Blast results. The Agene program (Munch and Krogh, 2006, *BMC Bioinformatics* 7: 263) and SignalP program (Nielsen et al., 1997, *Protein Engineering* 10: 1-6) were used to identify starting codons. The SignalP program was further used to predict signal peptide. Pepstats (Rice et al, 2000, *Trends Genet.* 16(6): 276-277) was used to predict isoelectric point and molecular weight of the deduced amino acid sequence.

Example 3

Cloning of the *Malbranchea cinnamomea* Catalase Gene from Genomic DNA

One catalase gene, cat_ZY582303_121 (SEQ ID NO: 1), was selected for expression cloning.

Based on DNA information (SEQ ID NO: 1) obtained from genome sequencing, oligonucleotide primers, shown below in Table 1, were designed to amplify the catalase gene from the genomic DNA of *Malbranchea cinnamomea* NN044758. Primers were synthesized by Invitrogen Beijing, China.

TABLE 1

| primers | | |
|---|---|---|
| Forward primer | ACACAACTGGGGATCC ACC atgccgaacctcgtacgg | SEQ ID NO: 9 |
| Reverse primer | GTCACCCTCTAGATCT gaag gtgcactactgaccttacac gag | SEQ ID NO: 10 |

Lowercase characters of the forward primer represent the coding regions of the gene and lowercase characters of the reverse primer represent the flanking region of the gene, while capitalized parts were homologous to the insertion sites of pPFJO355 vector which has been described in WO2011005867.

Twenty picomoles of each forward and reverse primer pair were used in a PCR reaction composed of 2 μl of *Malbranchea cinnamomea* NN044758 genomic DNA, 10 μl of 5×GC Buffer, 1.5 μl of dimethyl sulphoxide (DMSO), 2.5 mM each of dATP, dTTP, dGTP, and dCTP, and 0.6 unit of PHUSION™ High-Fidelity DNA Polymerase (Finnzymes Oy, Espoo, Finland) in a final volume of 50 μl. The amplification was performed using a Peltier Thermal Cycler (M J Research Inc., South San Francisco, Calif., USA) programmed for denaturing at 94° C. for 1 minute; 6 cycles of denaturing at 94° C. for 15 seconds, annealing at 68° C. for 30 seconds, with a 1° C. decrease per cycle and elongation at 72° C. for 100 seconds; and another 23 cycles each at 94° C. for 15 seconds, 65° C. for 30 seconds and 72° C. for 100 seconds; and a final extension at 72° C. for 5 minutes. The heat block then went to a 4° C. soak cycle.

The PCR product was isolated by 1.0% agarose gel electrophoresis using 90 mM Tris-borate and 1 mM EDTA (TBE) buffer where a single product band around the expected size, ~2.6 kb, was visualized under UV light. PCR product was then purified from solution by using an ILLUS- TRA® GFX® PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR DNA and Gel Band Purification Kit according to the manufacturer's instructions.

An IN-FUSION™ CF Dry-down Cloning Kit (Clontech Laboratories, Inc., Mountain View, Calif., USA) was used to clone the fragment directly into the expression vector pPFJO355, without the need for restriction digestion and ligation.

The PCR product and the digested vector were ligated together using an IN-FUSION™ CF Dry-down PCR Cloning Kit (Clontech Laboratories, Inc., Mountain View, Calif., USA) resulting in plasmid pCat_ZY582303_121 (FIG. 5) in which the transcription of *Malbranchea cinnamomea* catalase gene was under the control of a promoter from the gene for *Aspergillus oryzae* alpha-amylase. The cloning operation was conducted according to the manufacturer's instruction. In brief, for each ligation reaction 30 ng of pPFJO355 digested with Bam HI and Bgl II, and 60 ng of the purified *Malbranchea cinnamomea* catalase PCR products were added to the reaction vials and resuspended the powder in a final volume of 10 µl with addition of deionized water. The reaction was incubated at 37° C. for 15 minutes and then 50° C. for 15 minutes. Three microlitres of the reaction products were used to transform *E. coli* TOP10 competent cells (TIANGEN Biotech (Beijing) Co. Ltd., Beijing, China). *E. coli* transformants containing expression constructs were detected by colony PCR which is a method for quick screening of plasmid inserts directly from *E. coli* colonies. Briefly, in the premixed PCR solution aliquot in each PCR tube, including PCR buffer, $MgCl_2$, dNTP and primer pairs for which the PCR fragment generated, a single colony was added by picking up with a sterile tip and twirling the tip in the reaction solution. Normaly 7-10 colonies were screened. After the PCR program, reactions were checked on agarose gel. The colony giving the amplification of expected size was possibly to contain the correct insert. Plasmid DNA was prepared from colonies showing inserts with the expected sizes using a QIAprep® Spin Miniprep Kit (QIAGEN GmbH, Hilden, Germany). The *Malbranchea cinnamomea* catalase gene inserted in pCat_ZY582303_121 was confirmed by DNA sequencing using a 3730XL DNA Analyzer (Applied Biosystems Inc, Foster City, Calif., USA).

Example 4

Expression of *Malbranchea cinnamomea* catalase gene in *Aspergillus oryzae*

*Aspergillus oryzae* HowB101 (described in patent WO9535385 example 1) protoplasts were prepared according to the method of Christensen et al, 1988, *Bio/Technology* 6: 1419-1422 and transformed with 3 µg of pCat_ZY582303_121.

The transformation of *Aspergillus oryzae* HowB101 with pCat_ZY582303_121 yielded about 50 transformants for each transformation. Eight transformants were isolated to individual Minimal medium plates.

Four transformants from the transformation were inoculated separately into 3 ml of YPM medium in a 24-well plate and incubated at 30° C. with mixing at 150 rpm. After 3 days incubation, 20 µl of supernatant from each culture were analyzed by SDS-PAGE using a NUPAGE® NOVEX® 4-12% Bis-Tris Gel with 50 mM MES (Invitrogen Corporation, Carlsbad, Calif., USA) according to the manufacturer's instructions. The resulting gel was stained with INSTANTBLUE™ (Expedeon Ltd., Babraham Cambridge, UK). SDS-PAGE profiles of the cultures showed the expression with protein bands detected. The size of major band of the gene was around 80 kDa. The expression strain was designated as O6QZB.

Example 5

Fermentation of Expression Strain O6QZB

A slant of the expression strain, O6QZB, was washed with 10 ml of YPM medium and inoculated into eight 2-liter flasks, each containing 400 ml of YPM medium to generate broth. The culture was harvested on day 3 and filtered using a 0.45 µm DURAPORE® Membrane (Millipore, Bedford, Mass., USA).

Example 6

Purification of Recombinant Ma/Branchea Cinnamomea Catalase from *Aspergillus orzyae* O6QZB 3200 ml volume of filtered supernatant of the recombinant strain O6QZB (Example 5) was precipitated with ammonium sulfate (80% saturation), re-dissolved in 50 ml 20 mM Bis-Tris buffer, pH6.5, dialyzed against the same buffer, and filtered through a 0.45 µm filter. The final volume was 80 ml. The solution was applied to a 40 ml Q SEPHAROSE® Fast Flow column (GE Healthcare, Buckinghamshire, UK) equilibrated in 20 mM Bis-Tris buffer, pH6.5, and the proteins was eluted with a linear NaCl gradient (0-0.5M). Fractions eluted with 0.2-0.4M NaCl were collected and further purified on a 40 ml Phenyl Sepharose 6 Fast Flow column (GE 17-0965-05) with a linear $(NH_4)_2SO_4$ gradient (1.2-0 M). Fractions from the column were analyzed by SDS-PAGE using a NUPAGE® NOVEX® Bis-Tris Gel, 1.5MM15W. Fractions containing a band at approximately 80 kDa were pooled and concentrated by ultrafiltration.

Example 7

*Rhizomucor pusillus* Genomic DNA Extraction

*Rhizomucor pusillus* strain NN046782 was inoculated onto a PDA plate and incubated for 3 days at 45° C. in the darkness. Several mycelia-PDA plugs were inoculated into 500 ml shake flasks containing 100 ml of FG4 medium. The flasks were incubated for 3 days at 45° C. with shaking at 160 rpm. The mycelia were collected by filtration through MIRACLOTH® (Calbiochem, La Jolla, Calif., USA) and frozen under liquid nitrogen. Frozen mycelia were ground, by a mortar and a pestle, to a fine powder, and genomic DNA was isolated using DNeasy® Plant Maxi Kit (QIAGEN Inc., Valencia, Calif., USA) following the manufacturer's instruction.

Example 8

Genome Sequencing, Assembly and Annotation

The extracted genomic DNA samples were delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene identification and functional prediction. GeneID (Parra et al., 2000, *Genome Research* 10(4):511-515) was used for gene prediction. Blastall version 2.2.10 (Altschul et al, 1990, *J. Mol. Biol.* 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The catalases were identified by analysis of the Blast results. The Agene program (Munch and Krogh, 2006, *BMC Bioinformatics* 7: 263) and SignalP program (Nielsen et al., 1997, *Protein Engineering* 10: 1-6) were used to identify starting codons. The SignalP program was further used to predict the signal peptide. Pepstats (Rice et al., 2000, *Trends Genet.* 16(6): 276-277) was used to predict isoelectric points and molecular weights of the deduced amino acid sequences.

Example 9

Cloning of the *Rhizomucor pusillus* Catalase Genes from Genomic DNA

Two catalase genes, shown in Table 2, were selected for expression.

TABLE 2

| catalase genes | | |
|---|---|---|
| Gene name | DNA sequence | Protein sequence |
| cat_ZY654893_6661 | SEQ ID NO: 3 | SEQ ID NO: 4 |
| cat_ZY654878_5541 | SEQ ID NO: 5 | SEQ ID NO: 6 |

Based on DNA information (SEQ ID NO: 3 and SEQ ID NO: 5) obtained from genome sequencing, oligonucleotide primers, shown below in Table 3, were designed to amplify the catalase genes from the genomic DNA of *Rhizomucor pusillus* NN046782. Primers were synthesized by Invitrogen, Beijing, China.

TABLE 3

| primers | | |
|---|---|---|
| SEQID3_forward | ACACAACTGGGGATCC ACC atgcgactaggtgccttggca | SEQ ID NO: 11 |
| SEQID3_reverse | GTCACCCTCTAGATCT atcg attgagttgtacaagttcagc tacagc | SEQ ID NO: 12 |
| SEQID5_forward | ACACAACTGGGGATCC ACC atgaaagccggttcgcttctc | SEQ ID NO: 13 |
| SEQID5_reverse | GTCACCCTCTAGATCT cata tacgtaggactgggatgataa ctgtg | SEQ ID NO: 14 |

Lowercase characters of the forward primer represent the coding regions of the gene and lowercase characters of the reverse primer represent the flanking region of the gene, while capitalized parts were homologous to the insertion sites of pPFJO355 (WO2011005867).

For cat_ZY654893 6661, 20 picomoles of primer pair (SEQID3_forward and SEQID3_reverse) were used in a PCR reaction composed of 2 µl of *Rhizomucor pusillus* NN046782 genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplification was performed using a Peltier Thermal Cycler (M J Research Inc., South San Francisco, Calif., USA) programmed for denaturing at 98° C. for 1 minute; 6 cycles of denaturing at 98° C. for 30 seconds, annealing at 65° C. for 30 seconds, with a 1° C. decrease per cycle and elongation at 72° C. for 2.5 minutes; and another 25 cycles each at 94° C. for 30 seconds, 59° C. for 30 seconds and 72° C. for 2.5 minutes; and a final extension at 72° C. for 5 minutes. The heat block then went to a 4° C. soak cycle.

For cat_ZY654893 5541, 20 picomoles of primer pair (SEQID5_forward and SEQID5_reverse) were used in a PCR reaction composed of 2 µl of *Rhizomucor pusillus* NN046782 genomic DNA, 5 µl of 10×HIFI Buffer, 2 µl of 50 mM MgSO4, 2.5 mM each of dATP, dTTP, dGTP, and dCTP, and 2.5 units of PLATINUM® Taq DNA Polymerase High Fidelity (Invitrogen Corporation, Carlsbad, Calif., USA) in a final volume of 50 µl. The amplification was performed using a Peltier Thermal Cycler (M J Research Inc., South San Francisco, Calif., USA) programmed for denaturing at 94° C. for 1 minute; 6 cycles of denaturing at 94° C. for 15 seconds, annealing at 60° C. for 30 seconds, with a 1° C. decrease per cycle and elongation at 68° C. for 3 minutes; and another 23 cycles each at 94° C. for 15 seconds, 58° C. for 30 seconds and 68° C. for 3 minutes; and a final extension at 68° C. for 5 minutes. The heat block then went to a 4° C. soak cycle.

The PCR products were isolated by 1.0% agarose gel electrophoresis using 90 mM Tris-borate and 1 mM EDTA (TBE) buffer where a single product band of each reaction around the expected size, ~2.6 kb and ~2.8 kb for cat_ZY654893_6661 and cat_ZY654893_5541 respectively, was visualized under UV light. PCR products were then purified from solution by using an ILLUSTRA® GFX® PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR DNA and Gel Band Purification Kit according to the manufacturer's instructions.

An IN-FUSION™ CF Dry-down Cloning Kit (Clontech Laboratories, Inc., Mountain View, Calif., USA) was used to clone the fragment directly into the expression vector pPFJO355, without the need for restriction digestion and ligation.

TABLE 4

Figure 6:
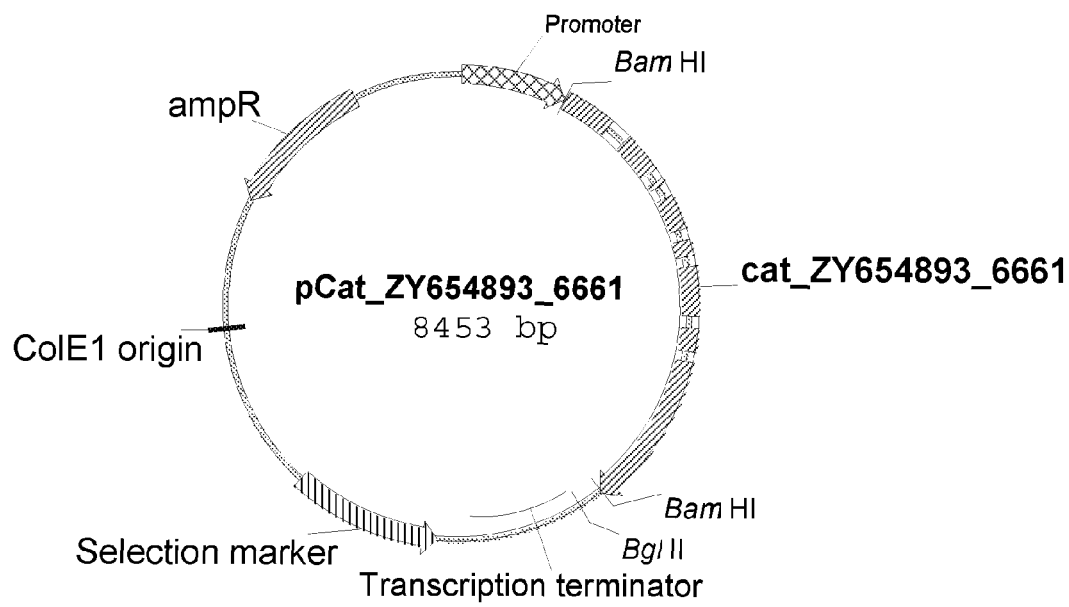
FIG. 6 shows a restriction map of pCat_ZY654893_6661.
Figure 7:
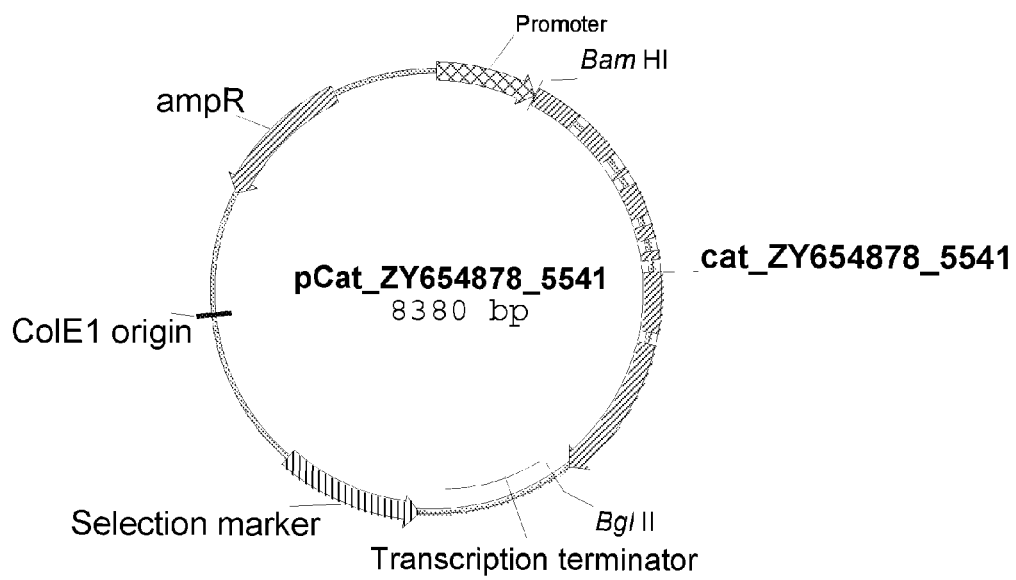
FIG. 7 shows a restriction map of pCat_ZY654878_5541.

| plasmids | | |
|---|---|---|
| Gene name | Plasmid | DNA map |
| cat_ZY654893_6661 | pCat_ZY654893_6661 | FIG. 6 |
| cat_ZY654878_5541 | pCat_ZY654878_5541 | FIG. 7 |

The PCR products and the digested vector were ligated together using an IN-FUSION™ CF Dry-down PCR Cloning resulting in plasmids shown in Table 4: pCat_ZY654893_6661 (FIG. 6) and pCat_ZY654878_5541 (FIG. 7), in which the transcription of *Ruzomucor pusillus* catalase genes was under the control of a promoter from the gene for *Aspergillus oryzae* alpha-amylase. The cloning operation was conducted according to the manufacturer's instruction. In brief, 30 ng of pPFJO355 digested with Bam HI and Bgl II, and 60 ng of the purified *Ruzomucor pusillus* catalase PCR products were added to the reaction vial and resuspended the powder in a final volume of 10 µl with addition of deionized water. The reaction product was incubated at 37° C. for 15 minutes and then 50° C. for 15 minutes. Three microlitres of the reaction were used to transform *E. coli* TOP10 competent cells (TIANGEN Biotech (Beijing) Co. Ltd., Beijing, China). *E. coli* transformants containing expression constructs were detected by colony PCR and plasmid DNA was prepared using a QIAprep® Spin Miniprep Kit (QIAGEN GmbH, Hilden, Germany). The *Ruzomucor pusillus* catalase genes inserted in pCat_ZY654893_6661 and pCat_ZY654878_5541 was confirmed by DNA sequencing using a 3730XL DNA Analyzer (Applied Biosystems Inc, Foster City, Calif., USA).

Example 10

*Penicillium emersonii* Genomic DNA Extraction

*Penicillium emersonii* strain NN051602 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen under liquid nitrogen. Frozen mycelia were ground, by a mortar and a pestle, to a fine powder, and genomic DNA was isolated using a Large-Scale Column Fungal DNAout (Baoman Biotechnology, Shanghai, China) according to the manufacturer's instructions.

Example 11

Genome Sequencing, Assembly and Annotation

The extracted genomic DNA samples were delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene identification and functional prediction. GeneID (Parra et al., 2000, *Genome Research* 10(4):511-515) was used for gene prediction. Blastall version 2.2.10 (Altschul et al., 1990, *J. Mol. Biol.* 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The catalase was identified by analysis of the Blast results. The Agene program (Munch and Krogh, 2006, *BMC Bioinformatics* 7: 263) and SignalP program (Nielsen et al., 1997, *Protein Engineering* 10: 1-6) were used to identify start codons. The SignalP program was further used to predict signal peptide. Pepstats (Rice et al., 2000, *Trends Genet.* 16(6): 276-277) was used to predict isoelectric point of proteins, and molecular weight of the deduced amino acid sequence.

Example 12

Cloning of the *Penicillium emersonii* Catalase from Genomic DNA

One catalase gene, PE04230007241 (SEQ ID NO: 7), was selected for expression cloning.

Based on the gene information (SEQ ID NO: 7) obtained by genome sequencing, oligonucleotide primers, shown below in Table 5, were designed to amplify the catalase gene, PE04230007241, from the genomic DNA of *Penicillium emersonii*. Primers were synthesized by Invitrogen, Beijing, China.

TABLE 5

| primers | | |
|---|---|---|
| Forward primer | 5' ACACAACTGGGGATCC ACC atgcgcgcagtgcag ct 3' | SEQ ID NO: 15 |
| Reverse primer | 5' GTCACCCTCTAGATCT gtcgactattccaaccttcct atatggacac 3' | SEQ ID NO: 16 |

Lowercase characters of the forward primer represent the coding regions of the gene and lowercase characters of the reverse primer represent the flanking region of the gene, while capitalized parts were homologous to the insertion sites of pPFJO355 vector which has been described in WO2011005867.

An IN-FUSION™ CF Dry-down Cloning Kit (Clontech Laboratories, Inc., Mountain View, Calif., USA) was used to clone the fragment directly into the expression vector pPFJO355, without the need for restriction digestion and ligation.

Twenty picomoles of each forward and reverse primer pair were used in a PCR reaction composed of 2 µl of *Penicillium emersonii* genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplification was performed using a Peltier Thermal Cycler (M J Research Inc., South San Francisco, Calif., USA) programmed for denaturing at 98° C. for 1 minute; 8 cycles of denaturing at 98° C. for 15 seconds, annealing at 65° C. for 30 seconds, with a 1° C. decrease per cycle and elongation at 72° C. for 3 minute 15 second; and another 22 cycles each at 98° C. for 15 seconds, 58 C for 30 seconds and 72° C. for 3 minute 15 second; and a final extension at 72° C. for 10 minutes. The heat block then went to a 4° C. soak cycle.

The reaction product was isolated by 1.0% agarose gel electrophoresis using 90 mM Tris-borate and 1 mM EDTA (TBE) buffer where a ~2.5 kb product band was excised from the gel, and purified using an ILLUSTRA® GFX® PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR DNA and Gel Band Purification Kit according to the manufacturer's instructions.

The PCR product and the digested vector were ligated together using an IN-FUSION™ CF Dry-down PCR Cloning kit resulting in pCat_PE04230007241 (FIG. 8) in which the transcription of the *Penicillium emersonii* catalase gene was under the control of a promoter from the gene for *Aspergillus oryzae* alpha-amylase. The cloning operation was conducted according to the manufacturer's instruction. In brief, 30 ng of pPFJO355 digested with Bam HI and Bgl II, and 60 ng of the purified *Penicillium emersonii* catalase gene PCR product were added to the reaction vials and resuspended the powder in a final volume of 10 µl with addition of deionized water. The reaction was incubated at 37° C. for 15 minutes and then 50° C. for 15 minutes. Three microlitres of the reaction were used to transform *E. coli* TOP10 competent cells (TIANGEN Biotech (Beijing) Co. Ltd., Beijing, China). An *E. coli* transformant containing pCat_PE04230007241 was detected by colony PCR. Colony PCR is a method for quick screening of plasmid inserts directly from *E. coli* colonies. Briefly, in the premixed PCR solution aliquot in each PCR tube, including PCR buffer, $MgCl_2$, dNTPs, and primer pairs from which the PCR fragment was generated, a single colony was added by picking with a sterile tip and twirling the tip in the reaction solution. Normally 7-10 colonies were screened. After the PCR, reactions were analyzed by 1.0% agarose gel electrophoresis using TBE buffer. Plasmid DNA was prepared from colonies showing inserts with the expected sizes using a QIAprep® Spin Miniprep Kit. The *Penicillium emersonii* catalase gene inserted in pCat_PE04230007241 was confirmed by DNA sequencing using a 3730XL DNA Analyzer (Applied Biosystems Inc, Foster City, Calif., USA).

Example 13

Expression of *Penicillium emersonii* Catalase Gene in *Aspergillus oryzae*

*Aspergillus oryzae* HowB101 (described in patent WO9535385 example 1) protoplasts were prepared according to the method of Christensen et al, 1988, *Bio/Technology* 6: 1419-1422 and transformed with 3 µg of pCat_PE04230007241.

The transformation of *Aspergillus oryzae* HowB101 with pCat_PE04230007241 yielded about 50 transformants. Four transformants were isolated to individual Minimal medium plates.

Four transformants were inoculated separately into 3 ml of YPM medium in a 24-well plate and incubated at 30° C., with mixing at 150 rpm. After 3 days incubation, 20 µl of supernatant from each culture were analyzed by SDS-PAGE using a NUPAGE® NOVEX® 4-12% Bis-Tris Gel with 50 mM MES (Invitrogen Corporation, Carlsbad, Calif., USA) according to the manufacturer's instructions. The resulting gel was stained with INSTANTBLUE™ (Expedeon Ltd., Babraham Cambridge, UK). SDS-PAGE profiles of the cultures showed that all transformants had a band of approximately 80 kDa. The expression strain was designated as O6YTS.

Example 14

Fermentation of *Aspergillus oryzae* Expression Strain O6YTS

A slant of the expression strain, O6YTS, was washed with 10 ml of YPM medium and inoculated into 7 2-liter flasks, each containing 400 ml of YPM medium to generate broth. The culture was harvested on day 3 and filtered using a 0.45 µm DURAPORE® Membrane (Millipore, Bedford, Mass., USA).

Example 15

Purification of Recombinant *Penicillium emersonii* Catalase from *Aspergillus Oryzae* O6YTS 2800 ml volume of filtered supernatant of the recombinant strain O6YTS (Example 14) was precipitated with ammonium sulfate (80% saturation), re-dissolved in 50 ml 20 mM Tris-HCl buffer, pH8.0, dialyzed against the same buffer, and filtered through a 0.45 µm filter. The final volume was 80 ml. The solution was applied to a 40 ml Q SEPHAROSE® Fast Flow column (GE Healthcare, Buckinghamshire, UK) equilibrated in 20 mM Tris-HCl buffer, pH8.0. Fractions eluted with 0.18-0.25M NaCl were analyzed by SDS-PAGE using a NUPAGE® NOVEX® 4-12% Bis-Tris Gel, 1.5MM15W. Fractions containing a band at approximately 80 kDa were pooled and concentrated by ultrafiltration.

Example 16

Characterization of the genomic DNAs encoding catalases

The genomic DNA sequence (SEQ ID NO: 1) and deduced amino acid sequence (SEQ ID NO: 2) of the *Malbranchea cinnamomea* catalase coding sequence is shown in FIG. 5. The coding sequence is 2622 bp including the stop codon and is interrupted by 6 introns of 81 bp (nucleotides 289 to 369), 69 bp (nucleotides 404 to 472), 72 bp (nucleotides 665 to 736), 68 bp (nucleotides 1153 to 1220), 71 bp (nucleotides 1386 to 1456) and 71 bp (nucleotides 1632 to 1702). The G+C content of the mature polypeptide coding sequence without introns and stop codon is 52.8%. The encoded predicted protein is 729 amino acids. Using the SignalP program (Nielsen et al., 1997, *Protein Engineering* 10: 1-6), a signal peptide of 16 residues was predicted. The predicted mature protein contains 713 amino acids with a predicted molecular weight of 79259.08 Dalton and predicted isoelectric point of 5.13. The catalase catalytic domain was predicted to be amino acids 17 to 723, by aligning the amino acid sequence using BLAST, where the single most significant alignment within a subfamily was used to predict the catalytic domain.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the mature part of amino acid sequence of the *Malbranchea cinnamomea* coding sequence encoding the catalase polypeptide shares 75.36% identity to the deduced amino acid sequence of catalase from *Neosartorya fischeri* (accession number UNIPROT:A1 DJU9).

The genomic DNA sequence (SEQ ID NO: 3) and deduced amino acid sequence (SEQ ID NO: 4) of the *Rhizomucor pusillus* catalase coding sequence is shown in FIG. 6. The coding sequence is 2711 bp including the stop codon and is interrupted by 7 introns of 124 bp (nucleotides 291 to 414), 64 bp (nucleotides 648 to 711), 77 bp (nucleotides 745 to 821), 67 bp (nucleotides 1021 to 1087), 58 bp (nucleotides 1179 to 1236), 70 bp (nucleotides 1520 to 1589) and 58 bp (nucleotides 1729 to 1786). The G+C content of the mature polypeptide coding sequence without introns and stop codon is 50%. The encoded predicted protein is 730 amino acids. Using the SignalP program (Nielsen et al., 1997, *Protein Engineering* 10: 1-6), a signal peptide of 20 residues was predicted. The predicted mature protein contains 710 amino acids with a predicted molecular weight of 79485.02 Dalton and predicted isoelectric point of 6.03. The catalase catalytic domain was predicted to be amino acids 38 to 723, by aligning the amino acid sequence using BLAST, where the single most significant alignment within a subfamily was used to predict the catalytic domain.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the mature part of amino acid sequence of the *Rhizomucor pusillus* coding sequence encoding the catalase polypeptide shares 53.67% identity to the catalase from *Bacillus pseudofirmus* (accession number UNIPROT: P30266).

The genomic DNA sequence (SEQ ID NO: 5) and deduced amino acid sequence (SEQ ID NO: 6) of the *Rhizomucor pusillus* catalase coding sequence is shown in FIG. 7. The coding sequence is 2673 bp including the stop codon and is interrupted by 7 introns of 72 bp (nucleotides 284 to 355), 100 bp (nucleotides 584 to 683), 75 bp (nucleotides 717 to 791), 57 bp (nucleotides 991 to 1047), 72 bp (nucleotides 1133 to 1204) and 72 bp (nucleotides 1259 to 1330) and 71 bp (nucleotides 1697 to 1767). The G+C content of the mature polypeptide coding sequence without introns and stop codon is 50.3%. The encoded predicted protein is 717 amino acids. Using the SignalP program (Nielsen et al., 1997, *Protein Engineering* 10: 1-6), a signal peptide of 24 residues was predicted. The predicted mature protein contains 693 amino acids with a predicted molecular weight of 77995.99 Dalton and predicted isoelectric point of 5.66. The catalase catalytic domain was predicted to be amino acids 38 to 711, by aligning the amino acid sequence using BLAST, where the single most significant alignment within a subfamily was used to predict the catalytic domain.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the mature part of amino acid sequence of the *Malbranchea cinnamomea* coding sequence encoding the catalase polypeptide shares 55.94% identity to the catalase from *Bacillus subtilis* (accession number UNIPROT: P42234).

Figure 8:
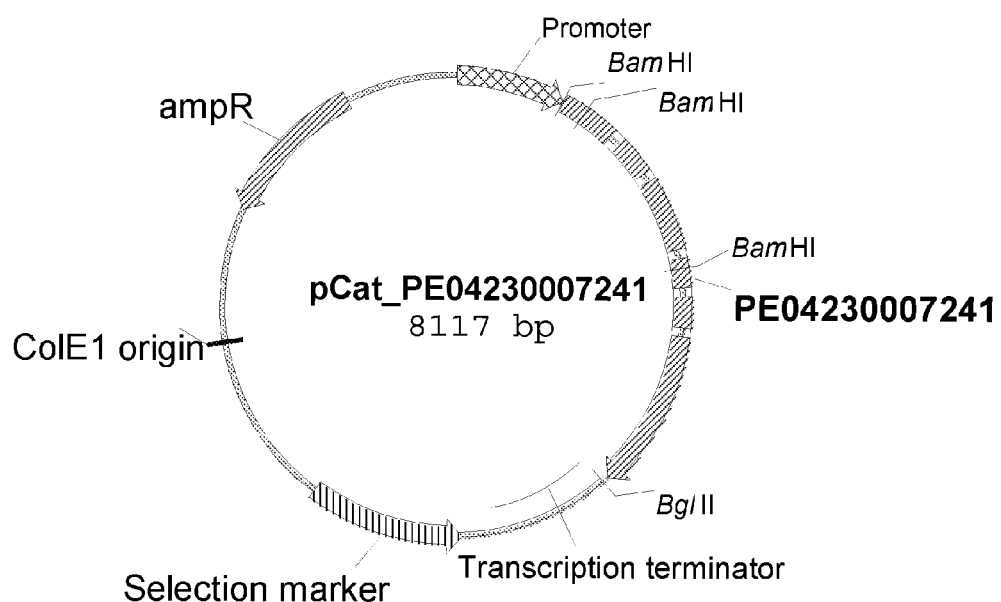
FIG. 8 shows a restriction map of pCat_PE04230007241.

The genomic DNA sequence (SEQ ID NO: 7) and deduced amino acid sequence (SEQ ID NO: 8) of the *Penicillium emersonii* catalase coding sequence is shown in FIG. 8. The coding sequence is 2479 bp including the stop codon and is interrupted by 5 introns of 53 bp (nucleotides 328 to 380), 50 bp (nucleotides 607 to 656), 51 bp (nucleotides 1073 to 1123), 52 bp (nucleotides 1289 to 1340), and 47 bp (nucleotides 1516 to 1562). The G+C content of the mature polypeptide coding sequence without introns and stop codon is 58.6%. The encoded predicted protein is 741 amino acids. Using the SignalP program (Nielsen et al., 1997, *Protein Engineering* 10: 1-6), a signal peptide of 19 residues was predicted. The predicted mature protein contains 722 amino acids with a predicted molecular weight of 79578.21 Dalton and predicted isoelectric point of 5.12. The catalase catalytic domain was predicted to be amino acids 20 to 740, by aligning the amino acid sequence using BLAST, where the single most significant alignment within a subfamily was used to predict the catalytic domain.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the mature part of amino acid sequence of the *Penicillium emersonii* coding sequence encoding the catalase polypeptide shares 82.38% identity to a catalase from *Thermoascus aurantiacus* (SEQ ID NO: 4 in JP2007143405-A)

Example 17

Catalase Activity Determination

Catalase activity was detected using 3% hydrogen peroxide as substrate. 3% hydrogen peroxide was prepared by 10 times dilution of 30% hydrogen peroxide with double distilled $H_2O$ (dd$H_2O$). 50 μl of 3% hydrogen peroxide was added to a well of the microtiter plate. Then 20 μl of purified catalase sample was added to the same well. The reaction was kept at room temperature for 10-30 seconds. The catalase activity was determined by observation of bubble (oxygen) generation.

As bubble (oxygen) generation was observed, *Malbranchea cinnamomea* catalase (Example 6) sample showed catalase activity and *Penicillium emersonii* catalase (Example 15) sample showed catalase activity.

Example 18

Catalase Activity Assay

The purified *Penicillium emersonii* catalase (Example 15) was checked for catalase activity by using the following protocol.

The substrate was prepared by 1000 times dilution of 30% $H_2O_2$ (from Xilong Chemical, Guangdong, China) with double distilled $H_2O$ (dd$H_2O$), the final concentration was 10.3 mM. The reaction was started by adding 1 μl of purified *Penicillium emersonii* catalase sample into 1000 μl of substrate. The optical density (OD) at 240 nm was read by Ultrospec 3300 (GE Healthcare, Buckinghamshire, UK) at second of 0 and 16 respectively, and the decrease of the OD (from 0.505 to 0.284) showed the relative activity of the *Penicillium emersonii* catalase.

Example 19

Boosting Effect of *Penicillium emersonii* Catalase on Hydrolysis of PCS

Corn stover was pretreated at the U.S. Department of Energy National Renewable Energy Laboratory (NREL) using dilute sulfuric acid at conditions of 190° C., 1 minute residence time, 0.05 g acid/g dry biomass, and at a 30% total solid concentration in a pretreatment reactor. Pretreated corn stover (PCS) was hydrolyzed at an initial total solid (TS) of 10% and total weight of hydrolysis system of 20 g. *Trichoderma reesei* cellulase composition (CELLIC® CTec2 available from Novozymes A/S, Bagsvaerd, Denmark) was added into the PCS for enzymatic hydrolysis. Five percent by weight of *Trichoderma reesei* cellulase composition was replaced with *P. emersonii* catalase based on protein amount and the total enzyme dose was 4 mg/g cellulose. The hydrolysis system with *Trichoderma reesei* cellulase composition but without catalase was used as a control. The flasks were incubated at 50° C. for 72 hours, with shaking at 130 rpm. After hydrolysis was completed, the sugar was analyzed by High Performance Liquid Chromatography (HPLC).

For HPLC measurement, the collected samples were filtered using 0.22 μm syringe filters (Millipore, Bedford, Mass., USA) and the filtrates were analyzed for sugar content as described below. The sugar concentrations of samples diluted in 0.005 M $H_2SO_4$ were measured using a 7.8×300 mm AMINEX® HPX-87H column (Bio-Rad Laboratories, Inc., Hercules, Calif., USA) by elution with 0.005 M $H_2SO_4$ at 65° C. at a flow rate of 0.7 ml per minute, and quantification by integration of the glucose signal from refractive index detection (CHEMSTATION®, AGILENT® 1100 HPLC, Agilent Technologies, Santa Clara, Calif., USA) calibrated by pure sugar samples. The resultant glucose was used to calculate the percentage of glucose yield from glucans for each reaction. Measured sugar concentrations were adjusted for the appropriate dilution factor. The net concentrations of enzymatically-produced sugars were determined by adjusting the measured sugar concentrations for corresponding background sugar concentrations in unwashed biomass at zero time point. All HPLC data processing was performed using MICROSOFT EXCEL™ software (Microsoft, Richland, Wash., USA).

The degree of glucose conversion to glucose was calculated according to the publication by Zhu, Y., et al. 2010, *Bioresource Technology*. 102(3): 2897-2903.

The results as shown in Table 6 demonstrated that PCS conversion to glucose can be improved significantly by adding small amounts of catalase.

TABLE 6

Effect of catalase from *P. emersonii* on glucose conversion of PCS.

|  | Control | *P. emersonii* Catalase |
| --- | --- | --- |
| Glucose conversion (%) | 48.6 ± 0.7 | 54.3 ± 0.8 |

The present invention is further described by the following numbered paragraphs:

[1] An isolated polypeptide having catalase activity, selected from the group consisting of:

(a) a polypeptides having at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8, a polypeptide having at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2, a polypeptides having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4, or a polypeptides having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6;

(b) a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 7, the mature polypeptide coding sequence of SEQ ID NO: 1, the mature polypeptide coding sequence of SEQ ID NO: 3, or the mature polypeptide coding sequence of SEQ ID NO: 5, (ii) the cDNA sequence thereof, or (iii) the full-length complement of (i) or (ii);

(c) a polypeptide encoded by a polynucleotide having at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7; or the cDNA sequence thereof, a polypeptide encoded by a polynucleotide having at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, a polypeptide encoded by a polynucleotide having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3, or a polypeptide encoded by a polynucleotide having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5;

(d) a variant of the mature polypeptide of SEQ ID NO: 8, a variant of the mature polypeptide of SEQ ID NO: 2, a variant of the mature polypeptide of SEQ ID NO: 4, or a variant of the mature polypeptide of SEQ ID NO: 6, comprising a substitution, deletion, and/or insertion at one or more (e.g., several) positions; and (e) a fragment of the polypeptide of (a), (b), (c), or (d) that has catalase activity.

[2] The polypeptide of paragraph 1, having at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8, having at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2, having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4, or having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6.

[3] The polypeptide of paragraph 1 or 2, which is encoded by a polynucleotide that hybridizes under low stringency conditions, low-medium stringency conditions, medium stringency conditions, medium-high stringency conditions, high stringency conditions, or very high stringency conditions with (i) the mature polypeptide coding sequence of SEQ ID NO: 7, the mature polypeptide coding sequence of SEQ ID NO: 1, the mature polypeptide coding sequence of SEQ ID NO: 3, or the mature polypeptide coding sequence of SEQ ID NO: 5, (ii) the cDNA sequence thereof, or (iii) the full-length complement of (i) or (ii). [4] The polypeptide of any of paragraphs 1-3, which is encoded by a polynucleotide having at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7, or the cDNA sequence thereof, which is encoded by a polynucleotide having at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, or the cDNA sequence thereof, which is encoded by a polynucleotide having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3, or the cDNA sequence thereof, or which is encoded by a polynucleotide having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5, or the cDNA sequence thereof.

[5] The polypeptide of any of paragraphs 1-4, comprising or consisting of SEQ ID NO: 8, SEQ ID NO: 2, SEQ ID NO: 4, or SEQ ID NO: 6, or the mature polypeptide of SEQ ID NO: 8, the mature polypeptide of SEQ ID NO: 2, the mature polypeptide of SEQ ID NO: 4, or the mature polypeptide of SEQ ID NO: 6.

[6] The polypeptide of paragraph 5, wherein the mature polypeptide is amino acids 20 to 741 of SEQ ID NO: 8, amino acids 17 to 729 of SEQ ID NO: 2, amino acids 21 to 730 of SEQ ID NO: 4, or amino acids 25 to 717 of SEQ ID NO: 6.

[7] The polypeptide of any of paragraphs 1-4, which is a variant of the mature polypeptide of SEQ ID NO: 8, a variant of the mature polypeptide of SEQ ID NO: 2, a variant of the mature polypeptide of SEQ ID NO: 4, or a variant of the mature polypeptide of SEQ ID NO: 6, comprising a substitution, deletion, and/or insertion at one or more (e.g., several) positions. [8] The polypeptide of paragraph 1, which is a fragment of SEQ ID NO: 8, SEQ ID NO: 2, SEQ ID NO: 4, or SEQ ID NO: 6, wherein the fragment has catalase activity.

[9] An isolated polypeptide comprising a catalytic domain selected from the group consisting of:

(a) a catalytic domain having at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to amino acids 20 to 740 of SEQ ID NO: 8; a catalytic domain having at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to amino acids 17 to 723 of SEQ ID NO: 2; a catalytic domain having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to amino acids 38 to 723 of SEQ ID NO: 4; or a catalytic domain having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to amino acids 38 to 711 of SEQ ID NO: 6;

(b) a polypeptide encoded by a polynucleotide that hybridizes under low, medium, medium-high, high, or very high stringency conditions with (i) nucleotides 58 to 2473 of SEQ ID NO: 7, nucleotides 49 to 2601 of SEQ ID NO: 1, nucleotides 112 to 2687 of SEQ ID NO: 3, or nucleotides 112 to 2652 of SEQ ID NO: 5, (ii) the cDNA sequence thereof, or (iii) the full-length complement of (i) or (ii);

(c) a catalytic domain encoded by a polynucleotide having at least 83%, e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 58 to 2473 of SEQ ID NO: 7; a catalytic domain encoded by a polynucleotide having at least 76%, e.g., at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 49 to 2601 of SEQ ID NO: 1; a catalytic domain encoded by a polynucleotide having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 112 to 2687 of SEQ ID NO: 3; or a catalytic domain encoded by a polynucleotide having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 112 to 2652 of SEQ ID NO: 5;

(d) a variant of amino acids 20 to 740 of SEQ ID NO: 8, a variant of amino acids 17 to 723 of SEQ ID NO: 2, a variant of amino acids 38 to 723 of SEQ ID NO: 4, or a variant of amino acids 38 to 711 of SEQ ID NO: 6, comprising a substitution, deletion, and/or insertion of one or more (e.g., several) positions; and (e) a fragment of a catalytic domain of (a), (b), (c), or (e) which has catalase activity.

[10] A composition comprising the polypeptide of any of paragraphs 1-9.

[11] An isolated polynucleotide encoding the polypeptide of any of paragraphs 1-9.

[12] A nucleic acid construct or expression vector comprising the polynucleotide of paragraph 11 operably linked to one or more (e.g., several) control sequences that direct the production of the polypeptide in an expression host.

[13] A recombinant host cell comprising the polynucleotide of paragraph 11 operably linked to one or more (e.g., several) control sequences that direct the production of the polypeptide.

[14] A method of producing the polypeptide of any of paragraphs 1-9, comprising:

(a) cultivating a cell, which in its wild-type form produces the polypeptide, under conditions conducive for production of the polypeptide; and optionally (b) recovering the polypeptide.

[15] A method of producing a polypeptide having catalase activity, comprising:

(a) cultivating the host cell of paragraph 13 under conditions conducive for production of the polypeptide; and optionally (b) recovering the polypeptide.

[16] A transgenic plant, plant part or plant cell transformed with a polynucleotide encoding the polypeptide of any of paragraphs 1-9.

[17] A method of producing a polypeptide having catalase activity, comprising:

(a) cultivating the transgenic plant or plant cell of paragraph 16 under conditions conducive for production of the polypeptide; and (b) recovering the polypeptide.

[18] A method of producing a mutant of a parent cell, comprising inactivating a polynucleotide encoding the polypeptide of any of paragraphs 1-9, which results in the mutant producing less of the polypeptide than the parent cell.

[19] A mutant cell produced by the method of paragraph 18.

[20] The mutant cell of paragraph 19, further comprising a gene encoding a native or heterologous protein.

[21] A method of producing a protein, comprising:

(a) cultivating the mutant cell of paragraph 19 or 20 under conditions conducive for production of the protein; and optionally (b) recovering the protein.

[22] A double-stranded inhibitory RNA (dsRNA) molecule comprising a subsequence of the polynucleotide of paragraph 11, wherein optionally the dsRNA is an siRNA or an miRNA molecule.

[23] The double-stranded inhibitory RNA (dsRNA) molecule of paragraph 22, which is about 15, 16, 17, 18, 19, 20, 21, 22, 23, 24, 25 or more duplex nucleotides in length.

[24] A method of inhibiting the expression of a polypeptide having catalase activity in a cell, comprising administering to the cell or expressing in the cell the double-stranded inhibitory RNA (dsRNA) molecule of paragraph 22 or 23.

[25] A cell produced by the method of paragraph 24.

[26] The cell of paragraph 25, further comprising a gene encoding a native or heterologous protein.

[27] A method of producing a protein, comprising:

(a) cultivating the cell of paragraph 25 or 26 under conditions conducive for production of the protein; and optionally (b) recovering the protein.

[28] An isolated polynucleotide encoding a signal peptide comprising or consisting of amino acids 1 to 19 of SEQ ID NO: 8, amino acids 1 to 16 of SEQ ID NO: 2, amino acids 1 to 20 of SEQ ID NO: 4, or amino acids 1 to 24 of SEQ ID NO: 6.

[29] A nucleic acid construct or expression vector comprising a gene encoding a protein operably linked to the polynucleotide of paragraph 28, wherein the gene is foreign to the polynucleotide encoding the signal peptide.

[30] A recombinant host cell comprising a gene encoding a protein operably linked to the polynucleotide of paragraph 28, wherein the gene is foreign to the polynucleotide encoding the signal peptide.

[31] A method of producing a protein, comprising:

(a) cultivating a recombinant host cell comprising a gene encoding a protein operably linked to the polynucleotide of paragraph 28, wherein the gene is foreign to the polynucleotide encoding the signal peptide, under conditions conducive for production of the protein; and optionally (b) recovering the protein.

[32] A process for degrading or converting a cellulosic material, comprising: treating the cellulosic material with an enzyme composition in the presence of the polypeptide having catalase activity of any of paragraphs 1-9.

[33] The process of paragraph 32, wherein the cellulosic material is pretreated.

[34] The process of paragraph 32 or 33, wherein the enzyme composition comprises one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[35] The process of paragraph 34, wherein the cellulase is one or more (e.g., several) enzymes selected from the group consisting of an endoglucanase, a cellobiohydrolase, and a beta-glucosidase.

[36] The process of paragraph 35, wherein the hemicellulase is one or more (e.g., several) enzymes selected from the group consisting of a xylanase, an acetylxylan esterase, a feruloyl esterase, an arabinofuranosidase, a xylosidase, and a glucuronidase.

[37] The process of any of paragraphs 32-36, further comprising recovering the degraded or converted cellulosic material.

[38] The process of paragraph 37, wherein the degraded cellulosic material is a sugar.

[39] The process of paragraph 38, wherein the sugar is selected from the group consisting of glucose, xylose, mannose, galactose, and arabinose.

[40] A process for producing a fermentation product, comprising:
(a) saccharifying a cellulosic material with an enzyme composition in the presence of the polypeptide having catalase activity of any of paragraphs 1-9;
(b) fermenting the saccharified cellulosic material with one or more (e.g., several) fermenting microorganisms to produce the fermentation product; and optionally
(c) recovering the fermentation product from the fermentation.

[41] The process of paragraph 40, wherein the cellulosic material is pretreated.

[42] The process of paragraph 40 or 41, wherein the enzyme composition comprises the enzyme composition comprises one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[43] The process of paragraph 42, wherein the cellulase is one or more (e.g., several) enzymes selected from the group consisting of an endoglucanase, a cellobiohydrolase, and a beta-glucosidase.

[44] The process of paragraph 42, wherein the hemicellulase is one or more (e.g., several) enzymes selected from the group consisting of a xylanase, an acetylxylan esterase, a feruloyl esterase, an arabinofuranosidase, a xylosidase, and a glucuronidase.

[45] The process of any of paragraphs 40-44, wherein steps (a) and optionally (b) are performed simultaneously in a simultaneous saccharification and fermentation.

[46] The process of any of paragraphs 40-45, wherein the fermentation product is an alcohol, an alkane, a cycloalkane, an alkene, an amino acid, a gas, isoprene, a ketone, an organic acid, or polyketide.

[47] A process of fermenting a cellulosic material, comprising: fermenting the cellulosic material with one or more (e.g., several) fermenting microorganisms, wherein the cellulosic material is saccharified with an enzyme composition in the presence of the polypeptide having catalase activity of any of paragraphs 1-9.

[48] The process of paragraph 47, wherein the fermenting of the cellulosic material produces a fermentation product.

[49] The process of paragraph 48, further comprising recovering the fermentation product from the fermentation.

[50] The process of any of paragraphs 47-49, wherein the cellulosic material is pretreated before saccharification.

[51] The process of any of paragraphs 47-50, wherein the enzyme composition comprises one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[52] The process of paragraph 51, wherein the cellulase is one or more (e.g., several) enzymes selected from the group consisting of an endoglucanase, a cellobiohydrolase, and a beta-glucosidase.

[53] The process of paragraph 51, wherein the hemicellulase is one or more (e.g., several) enzymes selected from the group consisting of a xylanase, an acetylxylan esterase, a feruloyl esterase, an arabinofuranosidase, a xylosidase, and a glucuronidase.

[54] The process of any of paragraphs 47-53, wherein the fermentation product is an alcohol, an alkane, a cycloalkane, an alkene, an amino acid, a gas, isoprene, a ketone, an organic acid, or polyketide.

[55] A whole broth formulation or cell culture composition comprising the polypeptide of any of paragraphs 1-9.

[56] A method for removing hydrogen peroxide, comprising treating a mixture to which hydrogen peroxide has been added or generated with the polypeptide of any of paragraphs 1-9.

[57] A method for generating molecular oxygen, comprising treating a mixture to which hydrogen peroxide has been added or generated with the polypeptide of any of paragraphs 1-9.

[58] A method for removing hydrogen peroxide from textile, comprising treating the textile with the polypeptide having catalase activity of any of paragraphs 1-9.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A process for degrading or hydrolyzing a cellulosic material, comprising: contacting the cellulosic material with a cellulolytic enzyme composition and an isolated polypeptide to thereby degrade or hydrolyze the cellulosic material, wherein said isolated polypeptide has catalase activity and is selected from the group consisting of:
   a) a polypeptide comprising an amino acid sequence having at least 95% sequence identity to the sequence of amino acids 20 to 741 of SEQ ID NO: 8, and
   b) a fragment of the sequence of amino acids 20 to 741 of SEQ ID NO: 8, wherein the fragment has catalase activity.

2. The process of claim 1, wherein said isolated polypeptide comprises an amino acid sequence having at least 97% sequence identity to the sequence of amino acids 20 to 741 of SEQ ID NO: 8.

3. The process of claim 1, wherein said isolated polypeptide comprises an amino acid sequence having at least 98% sequence identity to the sequence of amino acids 20 to 741 of SEQ ID NO: 8.

4. The process of claim 1, wherein said isolated polypeptide comprises an amino acid sequence having at least 99% sequence identity to the sequence of amino acids 20 to 741 of SEQ ID NO: 8.

5. The process of claim 1, wherein said isolated polypeptide comprises the sequence of amino acids 20 to 741 of SEQ ID NO: 8.

6. The process of claim 1, wherein said isolated polypeptide is encoded by a polynucleotide that hybridizes under high stringency conditions with the full-length complement of the nucleic acid sequence of nucleotides 58 to 2476 of SEQ ID NO: 7, wherein the high stringency conditions are defined as prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 2×SSC, 0.2% SDS at 65° C.

7. The process of claim 1, wherein said isolated polypeptide is encoded by a polynucleotide comprising a nucleic acid sequence having at least 95% sequence identity to the nucleic acid sequence of nucleotides 58 to 2476 of SEQ ID NO: 7.

8. The process of claim 1, wherein said isolated polypeptide is encoded by a polynucleotide comprising a nucleic acid sequence having at least 97% sequence identity to the nucleic acid sequence of nucleotides 58 to 2476 of SEQ ID NO: 7.

9. The process of claim 1, wherein said isolated polypeptide is encoded by a polynucleotide comprising a nucleic acid sequence having at least 99% sequence identity to the nucleic acid sequence of nucleotides 58 to 2476 of SEQ ID NO: 7.

10. The process of claim 1, wherein said isolated polypeptide is a variant of the sequence of amino acids 20 to 741 of SEQ ID NO: 8, wherein the variant is modified by a substitution, deletion, and/or insertion at one or more positions in the amino acid sequence of 20 to 741 of SEQ ID NO: 8, and wherein said isolated polypeptide comprises an amino acid sequence having at least 95% sequence identity to the sequence of amino acids 20 to 741 of SEQ ID NO: 8 and has catalase activity.

11. A process for producing a fermentation product, comprising:
   (a) saccharifying a cellulosic material with a cellulolytic enzyme composition and an isolated polypeptide to produce a saccharified cellulosic material, wherein the isolated polypeptide has catalase activity and is selected from the group consisting of:

i) a polypeptide comprising an amino acid sequence having at least 95% sequence identity to the sequence of amino acids 20 to 741 of SEQ ID NO: 8, and
   ii) a fragment of the sequence of amino acids 20 to 741 of SEQ ID NO: 8, wherein the fragment has catalase activity;
 (b) fermenting the saccharified cellulosic material with one or more fermenting microorganisms to produce the fermentation product; and optionally
 (c) recovering the fermentation product from the fermentation.

12. The process of claim 11, wherein said isolated polypeptide comprises an amino acid sequence having at least 97% sequence identity to the sequence of amino acids 20 to 741 of SEQ ID NO: 8.

13. The process of claim 11, wherein said isolated polypeptide comprises an amino acid sequence having at least 98% sequence identity to the sequence of amino acids 20 to 741 of SEQ ID NO: 8.

14. The process of claim 11, wherein said isolated polypeptide comprises an amino acid sequence having at least 99% sequence identity to the sequence of amino acids 20 to 741 of SEQ ID NO: 8.

15. The process of claim 11, wherein said isolated polypeptide comprises the sequence of amino acids 20 to 741 of SEQ ID NO: 8.

16. The process of claim 11, wherein said isolated polypeptide is encoded by a polynucleotide that hybridizes under high stringency conditions with the full-length complement of the nucleic acid sequence of nucleotides 58 to 2476 of SEQ ID NO: 7, wherein the high stringency conditions are defined as prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 2×SSC, 0.2% SDS at 65° C.

17. The process of claim 11, wherein said isolated polypeptide is encoded by a polynucleotide comprising a nucleic acid sequence having at least 95% sequence identity to the nucleic acid sequence of nucleotides 58 to 2476 of SEQ ID NO: 7.

18. The process of claim 11, wherein said isolated polypeptide is encoded by a polynucleotide comprising a nucleic acid sequence having at least 97% sequence identity to the nucleic acid sequence of nucleotides 58 to 2476 of SEQ ID NO: 7.

19. The process of claim 11, wherein said isolated polypeptide is encoded by a polynucleotide comprising a nucleic acid sequence having at least 99% sequence identity to the nucleic acid sequence of nucleotides 58 to 2476 of SEQ ID NO: 7.

20. The process of claim 11, wherein said isolated polypeptide is a variant of the sequence of amino acids 20 to 741 of SEQ ID NO: 8, wherein the variant is modified by a substitution, deletion, and/or insertion at one or more positions in the amino act sequence of 20 to 741 of SEQ ID NO: 8, and wherein said isolated polypeptide comprises an amino acid sequence having at least 95% sequence identity to the sequence of amino acids 20 to 741 of SEQ ID NO: 8 and has catalase activity.

* * * * *

SEQUENCE LISTING

```
<160> NUMBER OF SEQ ID NOS: 16

<210> SEQ ID NO 1
<211> LENGTH: 2650
<212> TYPE: DNA
<213> ORGANISM: Malbranchea cinnamomea

<400> SEQUENCE: 1
atgccgaacc tcgtacggct ccttgctctt gcgggagtcg tgtcggccgc ttgtccctac        60
ctttcagggg aattggacaa gcgtcaggct gactcgagca acgatgcagc tcaggctact       120
gaggaatttc tccagcagtt ctatctcaac gacaatgata catatatgac tactgacact       180
ggcaccccca ttgctgacca gcagagctta agcgtgggtg agagaggccc aacgctcctt       240
gaggacttta tcttccgcca gaaaatacag cgatttgacc atgagcgtgt atgtgacaaa       300
```

-continued

```
atcatgtgcc ttgccgcata ctctctcgtc cgtcacagat atggctaacg tgccgtcgaa      360
ttgatacagg ttcctgaacg tgctgtgcac gcacgcggag ctggtatgat gccacattcc      420
ttgtaaccca ccgttcagaa gttaatgcta aatggcactt tttcgacaat aggcgcccat      480
ggagttttca catcgtacgg agacttctcg aacatcactg ctgcttcgtt cctgtccgcg      540
gaaggcaaac agactcctgt atttgtccgt ttttccacgg ttgctggaag ccgtggtagc      600
tctgacatgg ctcgagacgt ccatggtttt gcaactcgat tctatactga cgaaggcaac      660
tttggtaagt cctctctctt gggcgaggat ggtcaatggt atagcacgtt tgattgactt      720
taattggtac ccgcagatat cgtcggaaac aacatcccgg tgttcttcat ccaggacgct      780
atccaattcc cggaccttat ccacgccgtg aagccaaagc aagataatga gatccctcaa      840
gcagccaccg cccacgattc tgcttgggac ttcttcagcc agcagcccag cacgatgcat      900
accttgatgt gggcaatggc aggacacggc atcccacgtt cataccgaca catggacggg      960
tttggtgtgc acaccttccg ttttgtgact gacgagggac agtcgaagct tgtcaagttc     1020
cacttcaaga ccttgcaagg aagggcttct atggtttggg aagaggcaca agtcatctcg     1080
gggaagaata cagattttca tagacaggac ctctttgagg caattgagtc cgggacttat     1140
ccagagtggg aggtatgcat ctgcatttcc atcctctctt agccttttct tgggtcccag     1200
gtgctgacct ttgtgtacag ttcggtgtcc aaattgttga tgaggaagat gagttgaaat     1260
ttggattcga cttgctcgac ccaaccaaga tcatccctga ggacttggtt cccgtcacac     1320
cgttgggaaa gctccagttg aaccggaacc ctcgcaacta ctttgctgaa actgagcagg     1380
ttatggtatg tcttgcattt cggtgaaatg cattctcgtt ggccgtaccg agagtctaac     1440 gaattttgt ttatagttcc aacctggtca cattgtccgt ggaatcgatt tcacagatga     1500
tcctctgctc caaggccgac tgttctccta ccttgacact cagctgaaca ggcatggtgg     1560
accaaatttc gagcagctcc ctatcaacca gcctcgagtc cctatccaca acaacaatcg     1620
tgatggtgcc ggtaggtttg atcaatcctt gtggcgatcc atttcccttg ctgtcaatgt     1680
ttctaacttt gtttcgaaac aggtcaaatg tacattcctc tgaaccccca tgcgtatagt     1740
cccaatactc tccacgctag ttcccctcgg caagccaacg agacccacgg caaaggtttc     1800
ttcactaccc ctggacgcac tccatctggc actctgcaac gatctctcag ccctacattt     1860
gcggatgtat ggtctcagcc acgtctcttc tacaactcac tacatcctgt ggaacgccaa     1920
ttcctggtga acgcgatcag gttcgagacg tcaaatctag ccagctcggt cgtacgcaag     1980
aatgtgatca tccagctcaa ccgaatttcc aacgacctgg cgagacgcgt ggcacggttt     2040
atcggcgttg aggaacctca gcctgatgaa aagttctacc acaacaacaa gacagtgccg     2100
cttggtactt tcggaacccc gttgaagtcg cttgctggtc tgaagattgg tattctctcc     2160
agtgtgaaca gctacgagga ggcgtcgcgc atcaagagtg cgttgcttga aaaggactcg     2220
agcgtcaagg tgtctgtcgt cgcggagaga ttggttcccg ggaggaggg cacagtggcc     2280 tacaccgcag ctgatggaac ttctttcgac ggtatcattg tgtcaaacgg cacggcggat     2340
ggtttcaccc cgtatgcctc gtctccgctc ttcccggctg ccggccact gcagatcctc     2400 gttgacgcat atcgctacgg caagcctgtt ggtgctattg gagatgctgg actcaaggcc     2460
ctcgacaatg ctggtatcca agaagctgag cgtgatgcgg agaagggtgt gttcacagcg     2520
tctgacgccg atgcaacctt cgtcgaggac tttctcgatg gattgaaggt gttccgattc     2580
cttgagcggt ttgatattga cgaagatgca gaggactact aggctcgtgt aaggtcagta     2640
gtgcaccttc                                                            2650
```

```
<210> SEQ ID NO 2
<211> LENGTH: 729
<212> TYPE: PRT
<213> ORGANISM: Malbranchea cinnamomea

<400> SEQUENCE: 2
```

| | | | | | | | | | | | | | | | |
|---|---|---|---|---|---|---|---|---|---|---|---|---|---|---|---|
| Met | Pro | Asn | Leu | Val | Arg | Leu | Leu | Ala | Leu | Ala | Gly | Val | Val | Ser | Ala |
| 1 | | | | 5 | | | | | 10 | | | | | 15 | |
| Ala | Cys | Pro | Tyr | Leu | Ser | Gly | Glu | Leu | Asp | Lys | Arg | Gln | Ala | Asp | Ser |
| | | | 20 | | | | | 25 | | | | | 30 | | |
| Ser | Asn | Asp | Ala | Ala | Gln | Ala | Thr | Glu | Glu | Phe | Leu | Gln | Gln | Phe | Tyr |
| | | 35 | | | | | 40 | | | | | 45 | | | |
| Leu | Asn | Asp | Asn | Asp | Thr | Tyr | Met | Thr | Thr | Asp | Thr | Gly | Thr | Pro | Ile |
| | 50 | | | | | 55 | | | | | 60 | | | | |
| Ala | Asp | Gln | Gln | Ser | Leu | Ser | Val | Gly | Glu | Arg | Gly | Pro | Thr | Leu | Leu |
| 65 | | | | | 70 | | | | | 75 | | | | | 80 |
| Glu | Asp | Phe | Ile | Phe | Arg | Gln | Lys | Ile | Gln | Arg | Phe | Asp | His | Glu | Arg |
| | | | | 85 | | | | | 90 | | | | | 95 | |
| Val | Pro | Glu | Arg | Ala | Val | His | Ala | Arg | Gly | Ala | Gly | Ala | His | Gly | Val |
| | | | 100 | | | | | 105 | | | | | 110 | | |
| Phe | Thr | Ser | Tyr | Gly | Asp | Phe | Ser | Asn | Ile | Thr | Ala | Ala | Ser | Phe | Leu |
| | | 115 | | | | | 120 | | | | | 125 | | | |
| Ser | Ala | Glu | Gly | Lys | Gln | Thr | Pro | Val | Phe | Val | Arg | Phe | Ser | Thr | Val |
| | 130 | | | | | 135 | | | | | 140 | | | | |
| Ala | Gly | Ser | Arg | Gly | Ser | Ser | Asp | Met | Ala | Arg | Asp | Val | His | Gly | Phe |
| 145 | | | | | 150 | | | | | 155 | | | | | 160 |
| Ala | Thr | Arg | Phe | Tyr | Thr | Asp | Glu | Gly | Asn | Phe | Asp | Ile | Val | Gly | Asn |
| | | | | 165 | | | | | 170 | | | | | 175 | |
| Asn | Ile | Pro | Val | Phe | Phe | Ile | Gln | Asp | Ala | Ile | Gln | Phe | Pro | Asp | Leu |
| | | | 180 | | | | | 185 | | | | | 190 | | |
| Ile | His | Ala | Val | Lys | Pro | Lys | Gln | Asp | Asn | Glu | Ile | Pro | Gln | Ala | Ala |
| | | 195 | | | | | 200 | | | | | 205 | | | |
| Thr | Ala | His | Asp | Ser | Ala | Trp | Asp | Phe | Phe | Ser | Gln | Gln | Pro | Ser | Thr |
| | 210 | | | | | 215 | | | | | 220 | | | | |
| Met | His | Thr | Leu | Met | Trp | Ala | Met | Ala | Gly | His | Gly | Ile | Pro | Arg | Ser |
| 225 | | | | | 230 | | | | | 235 | | | | | 240 |
| Tyr | Arg | His | Met | Asp | Gly | Phe | Gly | Val | His | Thr | Phe | Arg | Phe | Val | Thr |
| | | | | 245 | | | | | 250 | | | | | 255 | |
| Asp | Glu | Gly | Gln | Ser | Lys | Leu | Val | Lys | Phe | His | Phe | Lys | Thr | Leu | Gln |
| | | | 260 | | | | | 265 | | | | | 270 | | |
| Gly | Arg | Ala | Ser | Met | Val | Trp | Glu | Glu | Ala | Gln | Val | Ile | Ser | Gly | Lys |
| | | 275 | | | | | 280 | | | | | 285 | | | |
| Asn | Thr | Asp | Phe | His | Arg | Gln | Asp | Leu | Phe | Glu | Ala | Ile | Glu | Ser | Gly |
| | 290 | | | | | 295 | | | | | 300 | | | | |
| Thr | Tyr | Pro | Glu | Trp | Glu | Phe | Gly | Val | Gln | Ile | Val | Asp | Glu | Glu | Asp |
| 305 | | | | | 310 | | | | | 315 | | | | | 320 |
| Glu | Leu | Lys | Phe | Gly | Phe | Asp | Leu | Leu | Asp | Pro | Thr | Lys | Ile | Ile | Pro |
| | | | | 325 | | | | | 330 | | | | | 335 | |
| Glu | Asp | Leu | Val | Pro | Val | Thr | Pro | Leu | Gly | Lys | Leu | Gly | Leu | Asn | Arg |
| | | | 340 | | | | | 345 | | | | | 350 | | |
| Asn | Pro | Arg | Asn | Tyr | Phe | Ala | Glu | Thr | Glu | Gln | Val | Met | Phe | Gln | Pro |
| | | 355 | | | | | 360 | | | | | 365 | | | |
| Gly | His | Ile | Val | Arg | Gly | Ile | Asp | Phe | Thr | Asp | Asp | Pro | Leu | Leu | Gln |
| | 370 | | | | | 375 | | | | | 380 | | | | |

Gly Arg Leu Phe Ser Tyr Leu Asp Thr Gln Leu Asn Arg His Gly Gly
385                 390                 395                 400

Pro Asn Phe Glu Gln Leu Pro Ile Asn Gln Pro Arg Val Pro Ile His
            405                 410                 415

Asn Asn Asn Arg Asp Gly Ala Gly Gln Met Tyr Ile Pro Leu Asn Pro
            420                 425                 430

His Ala Tyr Ser Pro Asn Thr Leu His Ala Ser Ser Pro Arg Gln Ala
            435                 440                 445

Asn Glu Thr His Gly Lys Gly Phe Phe Thr Thr Pro Gly Arg Thr Pro
    450                 455                 460

Ser Gly Thr Leu Gln Arg Ser Leu Ser Pro Thr Phe Ala Asp Val Trp
465                 470                 475                 480

Ser Gln Pro Arg Leu Phe Tyr Asn Ser Leu His Pro Val Glu Arg Gln
            485                 490                 495

Phe Leu Val Asn Ala Ile Arg Phe Glu Thr Ser Asn Leu Ala Ser Ser
            500                 505                 510

Val Val Arg Lys Asn Val Ile Ile Gln Leu Asn Arg Ile Ser Asn Asp
            515                 520                 525

Leu Ala Arg Arg Val Ala Arg Phe Ile Gly Val Glu Glu Pro Gln Pro
530                 535                 540

Asp Glu Lys Phe Tyr His Asn Asn Lys Thr Val Pro Leu Gly Thr Phe
545                 550                 555                 560

Gly Thr Pro Leu Lys Ser Leu Ala Gly Leu Lys Ile Gly Ile Leu Ser
                565                 570                 575

Ser Val Asn Ser Tyr Glu Glu Ala Ser Arg Ile Lys Ser Ala Leu Leu
            580                 585                 590

Glu Lys Asp Ser Ser Val Lys Val Ser Val Val Ala Glu Arg Leu Val
            595                 600                 605

Pro Gly Glu Glu Gly Thr Val Ala Tyr Thr Ala Ala Asp Gly Thr Ser
            610                 615                 620

Phe Asp Gly Ile Ile Val Ser Asn Gly Thr Ala Asp Gly Phe Thr Pro
625                 630                 635                 640

Tyr Ala Ser Ser Pro Leu Phe Pro Ala Gly Arg Pro Leu Gln Ile Leu
                645                 650                 655

Val Asp Ala Tyr Arg Tyr Gly Lys Pro Val Gly Ala Ile Gly Asp Ala
            660                 665                 670

Gly Leu Lys Ala Leu Asp Asn Ala Gly Ile Gln Glu Ala Glu Arg Asp
            675                 680                 685

Ala Glu Lys Gly Val Phe Thr Ala Ser Asp Ala Asp Thr Phe Val
            690                 695                 700

Glu Asp Phe Leu Asp Gly Leu Lys Val Phe Arg Phe Leu Glu Arg Phe
705                 710                 715                 720

Asp Ile Asp Glu Asp Ala Glu Asp Tyr
                725

<210> SEQ ID NO 3
<211> LENGTH: 2846
<212> TYPE: DNA
<213> ORGANISM: Rhizomucor pusillus

<400> SEQUENCE: 3
atgcgactag gtgccttggc aaaccttctc gtcctctccc agttagcctt tgtaagaggc    60
gacgatgatc gcagcaacaa cgtctgtgcc ttccaagaac cagtatctgg agttggagcc   120
aatgcaaaga ccgagcagct caaactcttc accattaatg acgagggcac tcgggagaca   180

```
accaactttg gtgtcttggt caacaatagc gatagcttga aggcgggcta ccgcggccct     240
accctaatgg aagactttat gttgcgggaa aagataatgc actttggcaa gtaaaaatct     300
gtacaaaaat aaaaagcaaa ggatactaac gttcaagctg catccttata gatcatgaaa     360
ggtagctact atactgctga tgaagaaaat gcatataatt aacctctcta tcagaattcc     420
tgaacgcgtt gtacacgctc gaggtgtagc tgcccacggc tactttgaat catatgccga     480
ctggtcaagt ctcacagcag ccaagttcct gagcgctcca ggaaagcaga cacctacctt     540
tgtccgattc tctcccgtgc taggcagcaa aggttccgcg gacactgttc gcgatgatcg     600
tggtttcgct acacgcttct acaccgaaga aggcaatttc gatctaggtg atgcatagtc     660
tattgctaca agcctgcatc gaacctgtct ctcattcaat ttattcaata gttggcaaca     720
ttattgctcc attctttgtc caaggtatgt ttaagcaaac gatgaaaacc tttcgagtga     780
tgattctgat tgatatttaa atgcatatat cctcaaaata gatgctatca gtttcctga     840 tcttattcat gccgcaaaac cacaaccaga tactaatgtg ccgcaagcat caaccgctca     900
cgaaacggcg tatgactttt tcagtacgtt cccagagtcc atacacacag ttctctgggt     960
gctttctgga cgtggcattc cccgcagcct ccgccaagtc gaaggatttg gtatccacac    1020
gtaagtatcc atgttttgc aattagtaca cttttgcaat atccctaaca attcctatcc    1080
gttatagttt ccgtcttgtc aatgagaaag gcgagggtac gtttgtcaag tttatctgga    1140
aaccacatca aggtctttcg aatcttgctt gggcaagtgt tcaatattcg tggtatttga    1200
catcggaaaa tgcatttgct aacattaatt aaacagccag aagcacaaaa aatcagtggg    1260
attaacccgg atttccacca cgttgatttg actactgcta tcgaacgagg agattatccg    1320
gtttacgatc tctgcgtcca aatcataccc gaggaggacg aatttaaatt cgatttcgat    1380
ttactcgacc ccaccaagat tgtacctgag tccatagtac cagtcaccag gctcggaaag    1440
ctggtactca accggaaagt cgataacttc ttttcagaaa cggagcaagt aacttaccac    1500
gcaggccaca ttgttcgagg tatgattat ttgacaacaa aattttgcac caccagcggt    1560
gatttctaac gacgtcttcg tggcaacagg catcggcttt acagatgatc ccttgctcca    1620
aggccgtctc tttagctact tggatacaca gcttaatcgc atgagctcag ctaatttcct    1680
ccagctgcct atcaatcgac cgattactcc agtgcacaat aaccagcggt atcaacaact    1740
tgaacgatat ctaacgagtc aaccgactta ttttgctttt gtccagggac ggtttcatgc    1800
agtacaatgt gtacaagggt gccgtagcct acttcccgag ctcaataggc aaacctccag    1860
aagtgacgcc tccggagcaa ggtggctaca ttgaatatcc cgaaaaagtc aatggtatca    1920
aagttcgcgg ccgtctcca agcttctttg acttttactc gcatgcacag ctgttctgga    1980
actcgctcac agaagctgag cagcagcagc tcgtggacgc cagtcgtttc gagctcggca    2040
agtctcagtc gatggaagtc cgcaaacgaa tgattgatgt tttgaaccac gtcgacaatg    2100
gtctcgcgcg acgcgtcgct gtgggtatcg gcctcgagcc gcccgaaaag ttgtacgaaa    2160
accaaaacaa gacgagtgtt ggcttgtcca ttgaaaagta tccaaaaccg gacaatatcc    2220
gcactcgcac tgtggccatc ttgacagcac caggcacaaa cactcacgaa gctcaagcca    2280
tgtacgacta tctcaagcag gagggcgctt atcccgagta tatcggcatc catctaggaa    2340
aacaggacgg tctcaatatt acaaacacat atttgaccgc atcttctgtg ctctacgacg    2400
ctctctatgt tccgggtggc aaagaaggaa ttggcagact cacgaaacct tcgagtctat    2460
tcccgtatga ggagcccaag gtttggctgc tggatgcctg gagacacggc aaacctatca    2520
gcgcgtcagg cgaaggcatc aagctgctca aggcttccga tgtcaagatt cccaaagtca    2580
```

```
aagaaaatga ggtcacagag gcgcaaggag ttatcgtggg tccacctggg gatgacttga    2640
atcagaagta ccgctcggca cttgtacagc agcgcttctg gtatcgatta ccaatggatc    2700
ctcccattta actctttttc tttgcttcat gcaagaaata aaagcgatta cttttatatc    2760
atcgtattat tcagtatcta gcctttatca ttttttacag ttatgacatt aaaccgctgt    2820
agctgaactt gtacaactca atcgat                                         2846

<210> SEQ ID NO 4
<211> LENGTH: 730
<212> TYPE: PRT
<213> ORGANISM: Rhizomucor pusillus

<400> SEQUENCE: 4
```

Met Arg Leu Gly Ala Leu Ala Asn Leu Leu Val Leu Ser Gln Leu Ala
1               5                   10                  15

Phe Val Arg Gly Asp Asp Asp Arg Ser Asn Asn Val Cys Ala Phe Gln
            20                  25                  30

Glu Pro Val Ser Gly Val Gly Ala Asn Ala Lys Thr Glu Gln Leu Lys
        35                  40                  45

Leu Phe Thr Ile Asn Asp Glu Gly Thr Arg Glu Thr Thr Asn Phe Gly
    50                  55                  60

Val Leu Val Asn Asn Ser Asp Ser Leu Lys Ala Gly Tyr Arg Gly Pro
65                  70                  75                  80

Thr Leu Met Glu Asp Phe Met Leu Arg Glu Lys Ile Met His Phe Gly
                85                  90                  95

Lys Ile Pro Glu Arg Val Val His Ala Arg Gly Val Ala Ala His Gly
            100                 105                 110

Tyr Phe Glu Ser Tyr Ala Asp Trp Ser Ser Leu Thr Ala Ala Lys Phe
        115                 120                 125

Leu Ser Ala Pro Gly Lys Gln Thr Pro Thr Phe Val Arg Phe Ser Pro
    130                 135                 140

Val Leu Gly Ser Lys Gly Ser Ala Asp Thr Val Arg Asp Asp Arg Gly
145                 150                 155                 160

Phe Ala Thr Arg Phe Tyr Thr Glu Glu Gly Asn Phe Asp Leu Val Gly
                165                 170                 175

Asn Ile Ile Ala Pro Phe Phe Val Gln Asp Ala Ile Lys Phe Pro Asp
            180                 185                 190

Leu Ile His Ala Ala Lys Pro Gln Pro Asp Thr Asn Val Pro Gln Ala
        195                 200                 205

Ser Thr Ala His Glu Thr Ala Tyr Asp Phe Phe Ser Thr Phe Pro Glu
    210                 215                 220

Ser Ile His Thr Val Leu Trp Val Leu Ser Gly Arg Gly Ile Pro Arg
225                 230                 235                 240

Ser Leu Arg Gln Val Glu Gly Phe Gly Ile His Thr Phe Arg Leu Val
                245                 250                 255

Asn Glu Lys Gly Glu Gly Thr Phe Val Lys Phe Ile Trp Lys Pro His
            260                 265                 270

Gln Gly Leu Ser Asn Leu Ala Trp Ala Ser Pro Glu Ala Gln Lys Ile
        275                 280                 285

Ser Gly Ile Asn Pro Asp Phe His His Val Asp Leu Thr Thr Ala Ile
    290                 295                 300

Glu Arg Gly Asp Tyr Pro Val Tyr Asp Leu Cys Val Gln Ile Ile Pro
305                 310                 315                 320

```
Glu Glu Asp Glu Phe Lys Phe Asp Phe Asp Leu Leu Asp Pro Thr Lys
                325                 330                 335
Ile Val Pro Glu Ser Ile Val Pro Val Thr Arg Leu Gly Lys Leu Val
            340                 345                 350
Leu Asn Arg Lys Val Asp Asn Phe Phe Ser Glu Thr Glu Gln Val Thr
        355                 360                 365
Tyr His Ala Gly His Ile Val Arg Gly Ile Gly Phe Thr Asp Asp Pro
    370                 375                 380
Leu Leu Gln Gly Arg Leu Phe Ser Tyr Leu Asp Thr Gln Leu Asn Arg
385                 390                 395                 400
Met Ser Ser Ala Asn Phe Leu Gln Leu Pro Ile Asn Arg Pro Ile Thr
                405                 410                 415
Pro Val His Asn Asn Gln Arg Asp Gly Phe Met Gln Tyr Asn Val Tyr
            420                 425                 430
Lys Gly Ala Val Ala Tyr Phe Pro Ser Ser Ile Gly Lys Pro Pro Glu
        435                 440                 445
Val Thr Pro Pro Glu Gln Gly Gly Tyr Ile Glu Tyr Pro Glu Lys Val
    450                 455                 460
Asn Gly Ile Lys Val Arg Gly Arg Ser Pro Ser Phe Phe Asp Phe Tyr
465                 470                 475                 480
Ser His Ala Gln Leu Phe Trp Asn Ser Leu Thr Glu Ala Glu Gln Gln
                485                 490                 495
Gln Leu Val Asp Ala Ser Arg Phe Glu Leu Gly Lys Ser Gln Ser Met
            500                 505                 510
Glu Val Arg Lys Arg Met Ile Asp Val Leu Asn His Val Asp Asn Gly
        515                 520                 525
Leu Ala Arg Arg Val Ala Val Gly Ile Gly Leu Glu Pro Pro Glu Lys
    530                 535                 540
Leu Tyr Glu Asn Gln Asn Lys Thr Ser Val Gly Leu Ser Ile Glu Lys
545                 550                 555                 560
Tyr Pro Lys Pro Asp Asn Ile Arg Thr Arg Thr Val Ala Ile Leu Thr
                565                 570                 575
Ala Pro Gly Thr Asn Thr His Glu Ala Gln Ala Met Tyr Asp Tyr Leu
            580                 585                 590
Lys Gln Glu Gly Ala Tyr Pro Glu Tyr Ile Gly Ile His Leu Gly Lys
        595                 600                 605
Gln Asp Gly Leu Asn Ile Thr Asn Thr Tyr Leu Thr Ala Ser Ser Val
    610                 615                 620
Leu Tyr Asp Ala Leu Tyr Val Pro Gly Gly Lys Glu Gly Ile Gly Arg
625                 630                 635                 640
Leu Thr Lys Pro Ser Ser Leu Phe Pro Tyr Glu Pro Lys Val Trp
                645                 650                 655
Leu Leu Asp Ala Trp Arg His Gly Lys Pro Ile Ser Ala Ser Gly Glu
            660                 665                 670
Gly Ile Lys Leu Leu Lys Ala Ser Asp Val Lys Ile Pro Lys Val Lys
        675                 680                 685
Glu Asn Glu Val Thr Glu Ala Gln Gly Val Ile Val Gly Pro Pro Gly
    690                 695                 700
Asp Asp Leu Asn Gln Lys Tyr Arg Ser Ala Leu Val Gln Gln Arg Phe
705                 710                 715                 720
Trp Tyr Arg Leu Pro Met Asp Pro Pro Ile
                725                 730
```

<210> SEQ ID NO 5
<211> LENGTH: 2773
<212> TYPE: DNA
<213> ORGANISM: Rhizomucor pusillus

<400> SEQUENCE: 5

| | | | | | |
|---|---|---|---|---|---|
| atgaaagccg | gttcgcttct | cggaattgtt | gcaagcgttg | cactcttgct | ccagcagcaa | 60 |
| gtagcttttg | ctgaagaaac | atgcgctttt | caaaaccctg | ttggtgataa | cagcgaagat | 120 |
| gcgaaagccc | cccagctcaa | ggctttcaca | cgcaacgacg | ctggcactca | agaaactacg | 180 |
| aactttggtc | agcttgtaaa | caacacggac | agtttgaagg | ctggtttgcg | cggccctaca | 240 |
| ctgcttgaag | actttatgat | gcgtgaaaag | atcatgcact | tggtacgta | ttattgtatc | 300 |
| taaaccttca | attgattttg | tatttattgt | aaccgtgcaa | ttatctttcg | tgtagaccat | 360 |
| gaacgaattc | ccgagcgcgc | ggtacacgct | cgaggtgtcg | gtgcccacgg | ctactttgaa | 420 |
| ccctacgctg | actggggcaa | catcaccgct | gccaagttct | tgcgtgaacc | tggcaaaaga | 480 |
| acgccggtct | ttgtgcgatt | ctcgaccgtg | cttggttccc | gtggctcgcc | tgacactgtt | 540 |
| cgcgacgttc | gcggttttgc | tactcggttc | tacaccgagg | agggtttgtg | ggatctaggc | 600 |
| aagttttaa | ttcttttttc | ggtgtagaca | gaaactttat | tcttttttc | gagtgcaaga | 660 |
| acttataacc | gcgttgtata | tagtcggaaa | cgccattgca | ccgttctttg | tacagggtaa | 720 |
| gcttcccgat | gataggattt | gctgcttatc | cgtggtgaac | atttgctgat | gactactgct | 780 |
| attttacata | gacggtatca | agttcccaga | cttgatccac | gctggcaaac | cagagccaga | 840 |
| caaggaagtt | cctcaagccg | gtacagctca | cgaaactgcc | tatgatttct | tcgccgaatt | 900 |
| cccagaaact | ttgcacactg | ttttctgggc | tctctctggt | cgcggtattc | cgagaagttt | 960 |
| ccgtcaagtt | gaaggttttg | gtgtccatac | gtaagtctgg | ataaaccgat | tgcgttgctg | 1020 |
| cccattttgc | taactccaga | ccaccagatt | ccgattaatc | aacgaggaag | gcaagtctgt | 1080 |
| gtttgtcaag | ttccactgga | aacctctcca | gggtctctcc | aaccttgttt | gggtgagtta | 1140 |
| tttaaaacag | tcgttagtaa | cactatgtca | gtaagctaat | atataaatca | atcgttttga | 1200 |
| acaggatgaa | gcgcagaaga | tagctggaaa | ggatatcgat | ttccacagaa | cgatctggt | 1260 |
| gagtcttgga | catggacaaa | gaaaaatgtt | caccgaattg | tgtgattaac | tattcttgtt | 1320 |
| atacgctcag | tatactgcta | ttgagcgtgg | cgactatcca | gaatgggaac | tcggtgtaca | 1380 |
| gatcataccct | gaggaagacg | aagacaagtt | tgactttgat | ctcttggacc | ctaccaagat | 1440 |
| tgttcccgag | tctttggttc | ctgtgacgcg | tatcggcaag | atggtattaa | accgcaacgt | 1500 |
| taacaactac | ttttcggaga | cggagcaagt | taccttccac | cctggtcaca | ttgttcgcgg | 1560 |
| tattggcttt | accaacgatc | ctttgcttca | aggccgtctg | ttcagttact | tggacacaca | 1620 |
| gttgaaccgt | atgaactcgg | ccaatttcat | gcaaatcccc | atcaaccgac | ctatcaacgc | 1680 |
| tgtgcacaat | aaccaggtaa | atttcaatag | gcctgacttt | cattgttacc | attcccgtaa | 1740 |
| cttaaccatg | gtatttcttg | tgaaaagagg | gacggctacc | tccaaatgaa | cacgtttacc | 1800 |
| ggcaatgtcg | cctaccaccc | gaatggtctc | caacgtaaca | cgccttcgat | ggtcgaccct | 1860 |
| gaccaaggtg | gatacattga | ctatccggag | gaaatccatg | gcaaaaagca | acgtggacgc | 1920 |
| agcgccaaat | tctttgatta | ctactcgcaa | gctcaactgt | tctacaactc | tctgaccccg | 1980 |
| gctgagaagc | aacagatgat | cgatggtctc | cgcttcgaga | taggcaagtc | caagtcgctg | 2040 |
| gacgttcgca | agcgtatgat | caatgtcatc | aatcatgtcg | ataacgacct | tgctcgtcgt | 2100 |
| atcgctaagt | ctatcaatgt | ccccttgccc | gaaaaaattg | tcgagaacaa | gaaccagacg | 2160 |

-continued

```
tccactggtc tttccattga attgtatccc aaacctgaca acattcgcac ccgcacggtc    2220
gctattctga cagctccagg taccaatacc gaagaagcta aggccatgta tgactatctt    2280
gcttcggaag gtgcctacgt tgactatgtc ggtgttaacc tcggtgatca aggcggtctg    2340
aacattactg ctacgtatct gcataccctcg tctgtccttt acgatgctct ctacgtcccc    2400
ggcggtgaaa agggtatcaa ggtcttgtca gacaatgtga gcgagttccc gtacgatgaa    2460
cccaaggtct ttgttctcga tgcctatcgc acggaaagc ctattgcagc ttccagcgaa     2520
ggtgtcaagt ttatcaactc tgccgtcaat atggatatcc aagacaagga cggtgtagtc    2580
actgggtccg ctggcagcga cctccaaaca gaattcaaga aagcgctcat ccagcagcga    2640
ttctggtcac gattgccgct tgatcgtgac taaagtatat agaatatctc ttaggagtta    2700
atggtaacga taatgataat aataaacatt cattttcgta attcacagtt atcatcccag    2760
tcctacgtat atg                                                      2773
```

<210> SEQ ID NO 6
<211> LENGTH: 717
<212> TYPE: PRT
<213> ORGANISM: Rhizomucor pusillus

<400> SEQUENCE: 6

```
Met Lys Ala Gly Ser Leu Leu Gly Ile Val Ala Ser Val Ala Leu Leu
1               5                   10                  15

Leu Gln Gln Val Ala Phe Ala Glu Glu Thr Cys Ala Phe Gln Asn
            20                  25                  30

Pro Val Gly Asp Asn Ser Glu Asp Ala Lys Ala Ala Gln Leu Lys Ala
        35                  40                  45

Phe Thr Arg Asn Asp Ala Gly Thr Gln Glu Thr Thr Asn Phe Gly Gln
    50                  55                  60

Leu Val Asn Asn Thr Asp Ser Leu Lys Ala Gly Leu Arg Gly Pro Thr
65                  70                  75                  80

Leu Leu Glu Asp Phe Met Met Arg Glu Lys Ile Met His Phe Asp His
                85                  90                  95

Glu Arg Ile Pro Glu Arg Ala Val His Ala Arg Gly Val Gly Ala His
            100                 105                 110

Gly Tyr Phe Glu Pro Tyr Ala Asp Trp Gly Asn Ile Thr Ala Ala Lys
        115                 120                 125

Phe Leu Arg Glu Pro Gly Lys Arg Thr Pro Val Phe Val Arg Phe Ser
    130                 135                 140

Thr Val Leu Gly Ser Arg Gly Ser Pro Asp Thr Val Arg Asp Val Arg
145                 150                 155                 160

Gly Phe Ala Thr Arg Phe Tyr Thr Glu Glu Val Gly Asn Ala Ile Ala
                165                 170                 175

Pro Phe Phe Val Gln Asp Gly Ile Lys Phe Pro Asp Leu Ile His Ala
            180                 185                 190

Gly Lys Pro Glu Pro Asp Lys Glu Val Pro Gln Ala Gly Thr Ala His
        195                 200                 205

Glu Thr Ala Tyr Asp Phe Phe Ala Glu Phe Pro Glu Thr Leu His Thr
    210                 215                 220

Val Phe Trp Ala Leu Ser Gly Arg Gly Ile Pro Arg Ser Phe Arg Gln
225                 230                 235                 240

Val Glu Gly Phe Gly Val His Thr Phe Arg Leu Ile Asn Glu Glu Gly
                245                 250                 255
```

```
Lys Ser Val Phe Val Lys Phe His Trp Lys Pro Leu Gln Gly Leu Ser
            260                 265                 270

Asn Leu Val Trp Asp Glu Ala Gln Lys Ile Ala Gly Lys Asp Ile Asp
        275                 280                 285

Phe His Arg Asn Asp Leu Tyr Thr Ala Ile Glu Arg Gly Asp Tyr Pro
    290                 295                 300

Glu Trp Glu Leu Gly Val Gln Ile Ile Pro Glu Glu Asp Glu Asp Lys
305                 310                 315                 320

Phe Asp Phe Asp Leu Leu Asp Pro Thr Lys Ile Val Pro Glu Ser Leu
                325                 330                 335

Val Pro Val Thr Arg Ile Gly Lys Met Val Leu Asn Arg Asn Val Asn
            340                 345                 350

Asn Tyr Phe Ser Glu Thr Glu Gln Val Thr Phe His Pro Gly His Ile
        355                 360                 365

Val Arg Gly Ile Gly Phe Thr Asn Asp Pro Leu Leu Gln Gly Arg Leu
    370                 375                 380

Phe Ser Tyr Leu Asp Thr Gln Leu Asn Arg Met Asn Ser Ala Asn Phe
385                 390                 395                 400

Met Gln Ile Pro Ile Asn Arg Pro Ile Asn Ala Val His Asn Asn Gln
                405                 410                 415

Arg Asp Gly Tyr Leu Gln Met Asn Thr Phe Thr Gly Asn Val Ala Tyr
            420                 425                 430

His Pro Asn Gly Leu Gln Arg Asn Thr Pro Ser Met Val Asp Pro Asp
        435                 440                 445

Gln Gly Gly Tyr Ile Asp Tyr Pro Glu Glu Ile His Gly Lys Lys Gln
    450                 455                 460

Arg Gly Arg Ser Ala Lys Phe Phe Asp Tyr Tyr Ser Gln Ala Gln Leu
465                 470                 475                 480

Phe Tyr Asn Ser Leu Thr Pro Ala Glu Lys Gln Gln Met Ile Asp Gly
                485                 490                 495

Leu Arg Phe Glu Ile Gly Lys Ser Lys Ser Leu Asp Val Arg Lys Arg
            500                 505                 510

Met Ile Asn Val Ile Asn His Val Asp Asn Asp Leu Ala Arg Arg Ile
        515                 520                 525

Ala Lys Ser Ile Asn Val Pro Leu Pro Glu Lys Ile Val Glu Asn Lys
    530                 535                 540

Asn Gln Thr Ser Thr Gly Leu Ser Ile Glu Leu Tyr Pro Lys Pro Asp
545                 550                 555                 560

Asn Ile Arg Thr Arg Thr Val Ala Ile Leu Thr Ala Pro Gly Thr Asn
                565                 570                 575

Thr Glu Glu Ala Lys Ala Met Tyr Asp Tyr Leu Ala Ser Glu Gly Ala
            580                 585                 590

Tyr Val Asp Tyr Val Gly Val Asn Leu Gly Asp Gln Gly Gly Leu Asn
        595                 600                 605

Ile Thr Ala Thr Tyr Leu His Thr Ser Ser Val Leu Tyr Asp Ala Leu
    610                 615                 620

Tyr Val Pro Gly Gly Glu Lys Gly Ile Lys Val Leu Ser Asp Asn Val
625                 630                 635                 640

Ser Glu Phe Pro Tyr Asp Glu Pro Lys Val Phe Val Leu Asp Ala Tyr
                645                 650                 655

Arg His Gly Lys Pro Ile Ala Ala Ser Ser Glu Gly Val Lys Phe Ile
            660                 665                 670
```

-continued

```
Asn Ser Ala Val Asn Met Asp Ile Gln Asp Lys Asp Gly Val Val Thr
        675                 680                 685
Gly Ser Ala Gly Ser Asp Leu Gln Thr Glu Phe Lys Lys Ala Leu Ile
    690                 695                 700
Gln Gln Arg Phe Trp Ser Arg Leu Pro Leu Asp Arg Asp
705                 710                 715

<210> SEQ ID NO 7
<211> LENGTH: 2479
<212> TYPE: DNA
<213> ORGANISM: Penicillium emersonii

<400> SEQUENCE: 7
```

| | | |
|---|---|---|
| atgcgcgcag tgcagcttct gcccagcctc gccggcctga ttggcgctgc ctctgccgtt | 60 |
| ggatgtccgt atctgacggg ccagctcgat gccagagacg tgcacaatcc gcacgagttc | 120 |
| cagcgtcgac aggatcccgg agatgcggct gcgtccacag agcagttcct gtcccagttc | 180 |
| tatctcaatg acagcaacag ctacatgacc actgatgtcg gcggcccat ctcggatcag | 240 |
| aacagtttga aggccggaga gcgcggtcca accctgttgg aggacttcat cttccgtcag | 300 |
| aagatccagc actttgatca cgagcgggta ggttgtacca tccatgcgag agagatcgat | 360 |
| cgatgttgac gtggtggcag gtcccagaac gcgcagtcca tgctcgagga gccggcgccc | 420 |
| acggaacgtt cacttcctac ggaaactggt ccaacatcac tgcggcctcc ttcctgagcg | 480 |
| ctgaagggaa ggagaccccc gtgtttgtgc gcttctccac cgtggccgga agtcgaggca | 540 |
| gtgcggacac ggcgcgcgat gtgcatggct tgccaccag gttctacact gacgagggca | 600 |
| actttggtac gtcgtctcac aatcctctcg actggcatcg tctgaccgct gagcagatat | 660 |
| cgtcggcaac aacattccag tcttcttcat ccaggacgcc attctcttcc ctgatctgat | 720 |
| ccatgctgtc aagcccagcc ccgacaacga gatccccag gctgcgactg ctcatgacac | 780 |
| ggcctgggac ttcttcagcc agcagcccag tgcgttgcac acgctcttct gggctatgtc | 840 |
| cggccatgga atccctcgct cttttcgcca catggacggc tttggcgtcc acactttccg | 900 |
| attcgtgact gacgacggcg cctccaagct ggtcaaattc cactggacct cgctgcaggg | 960 |
| ccgggccagc ctggtctggg aggaggcgca agcggcagcg ggaaagaacc tggactatat | 1020 |
| gcgccaggac ctctatgaca catcgaagc cggtcgatat cctgaatggg aggtaggtgg | 1080 |
| ccgcattttc tcggcatata tatgtccatg ctgacgttcc tagctgggca ttcaaatcgt | 1140 |
| cgacgaggag gatcagctca gtttggatt tgatctgctg gatccaacca agatcattcc | 1200 |
| tgttgaatat gtccccatca cgccgcttgg gaagctgcag ctcaaccgga tccgctcaa | 1260 |
| ctatttcgcc gagacggagc agataatggt atgtaaacag tttgttgttc gattctttgc | 1320 |
| agtagactga cgatacatag ttccaacccg gccatattgt gcgcggaatt gactttaccg | 1380 |
| aagacccct tctccaggga cggctcttct cctatctcga cacgcagttg aatcggaatg | 1440 |
| gaggcccaa tttcgagcag cttcccatca atcgtcctag ggtgccatgg cataacaaca | 1500 |
| accgtgatgg attcagtaag tttaccccc tgcgctgact ctctgcatgc taactccacc | 1560 |
| aggccaagcg tttatccccc tgaacaaggc ggcctacagc ccgaacacgc tcaacaatgg | 1620 |
| caaccccaag caggcgaacc agactgtggg cgatggattc ttcaccactc ccggacgtac | 1680 |
| gaccagtggc cggctcatgc gcaccgtcag ttcgaccttc ccgacgtct ggtcgcagcc | 1740 |
| tcggctgttc tacaactcgc tggtgccggc cgagcagcag ttcctcgtca cgccatccg | 1800 |
| tttcgagaac tccaacgtca agagcgaagt ggtccggaac aatgtcatca tccagctcaa | 1860 |

```
ccgcgtcgat aacgacctcg cccgccgggt tgctcgggtc attggcgttg cagaacccga    1920
gcccgatcca acctattatc acaacaacaa gacggccaac gtgggtacgt ttggcacgcc    1980
gctcaagcgg atcgacggtc tcaaagtcgg tgtgcttgcc acagttggcg acccagacag    2040
tatcagtcag ggccagagcc tcagtgacgc gctctcggac tccaaggtcg atgtcactgt    2100
cgttgctgag tctttcacgg acggggtcga tgcgctctac accaactcgg acgcgaccgg    2160
cttcgacgcc gttatcgtgg ctgatggcgc cgaagggctt tttacccga gtagcttcac     2220 agccaaaccg acgaactcat tctcgacgac aacgctttat ccggccggtc gtccgctgca    2280
gatcctggtc gacgccttcc ggttcggcaa gcccgtcggc gctctgggca gcggagctaa    2340
ggcgcttgat gcggcaggta tctcgactag ccggcctggt gtgtacgtcg ccaactcgac    2400
cagcgaggcg ttcacggacg atatcgagga tggtttgcga acgttcaagt cctcgaccg    2460 gtttgcgctg gatgagtga                                                 2479
```

<210> SEQ ID NO 8
<211> LENGTH: 741
<212> TYPE: PRT
<213> ORGANISM: Penicillium emersonii

<400> SEQUENCE: 8

```
Met Arg Ala Val Gln Leu Leu Pro Ser Leu Ala Gly Leu Ile Gly Ala
1               5                   10                  15

Ala Ser Ala Val Gly Cys Pro Tyr Leu Thr Gly Gln Leu Asp Ala Arg
            20                  25                  30

Asp Val His Asn Pro His Glu Phe Gln Arg Arg Gln Asp Pro Gly Asp
        35                  40                  45

Ala Ala Ser Thr Glu Gln Phe Leu Ser Gln Phe Tyr Leu Asn Asp
    50                  55                  60

Ser Asn Ser Tyr Met Thr Thr Asp Val Gly Gly Pro Ile Ser Asp Gln
65              70                  75                  80

Asn Ser Leu Lys Ala Gly Glu Arg Gly Pro Thr Leu Leu Glu Asp Phe
                85                  90                  95

Ile Phe Arg Gln Lys Ile Gln His Phe Asp His Glu Arg Val Pro Glu
            100                 105                 110

Arg Ala Val His Ala Arg Gly Ala Gly Ala His Gly Thr Phe Thr Ser
        115                 120                 125

Tyr Gly Asn Trp Ser Asn Ile Thr Ala Ala Ser Phe Leu Ser Ala Glu
    130                 135                 140

Gly Lys Glu Thr Pro Val Phe Val Arg Phe Ser Thr Val Ala Gly Ser
145                 150                 155                 160

Arg Gly Ser Ala Asp Thr Ala Arg Asp Val His Gly Phe Ala Thr Arg
                165                 170                 175

Phe Tyr Thr Asp Glu Gly Asn Phe Asp Ile Val Gly Asn Asn Ile Pro
            180                 185                 190

Val Phe Phe Ile Gln Asp Ala Ile Leu Phe Pro Asp Leu Ile His Ala
        195                 200                 205

Val Lys Pro Ser Pro Asp Asn Glu Ile Pro Gln Ala Ala Thr Ala His
    210                 215                 220

Asp Thr Ala Trp Asp Phe Phe Ser Gln Gln Pro Ser Ala Leu His Thr
225                 230                 235                 240

Leu Phe Trp Ala Met Ser Gly His Gly Ile Pro Arg Ser Phe Arg His
                245                 250                 255
```

```
Met Asp Gly Phe Gly Val His Thr Phe Arg Phe Val Thr Asp Asp Gly
            260                 265                 270

Ala Ser Lys Leu Val Lys Phe His Trp Thr Ser Leu Gln Gly Arg Ala
        275                 280                 285

Ser Leu Val Trp Glu Glu Ala Gln Ala Ala Gly Lys Asn Leu Asp
    290                 295                 300

Tyr Met Arg Gln Asp Leu Tyr Asp Asn Ile Glu Ala Gly Arg Tyr Pro
305                 310                 315                 320

Glu Trp Glu Leu Gly Ile Gln Ile Val Asp Glu Asp Gln Leu Lys
                325                 330                 335

Phe Gly Phe Asp Leu Leu Asp Pro Thr Lys Ile Ile Pro Val Glu Tyr
            340                 345                 350

Val Pro Ile Thr Pro Leu Gly Lys Leu Gln Leu Asn Arg Asn Pro Leu
        355                 360                 365

Asn Tyr Phe Ala Glu Thr Glu Gln Ile Met Phe Gln Pro Gly His Ile
    370                 375                 380

Val Arg Gly Ile Asp Phe Thr Glu Asp Pro Leu Leu Gln Gly Arg Leu
385                 390                 395                 400

Phe Ser Tyr Leu Asp Thr Gln Leu Asn Arg Asn Gly Gly Pro Asn Phe
            405                 410                 415

Glu Gln Leu Pro Ile Asn Arg Pro Arg Val Pro Trp His Asn Asn Asn
        420                 425                 430

Arg Asp Gly Phe Ser Gln Ala Phe Ile Pro Leu Asn Lys Ala Ala Tyr
    435                 440                 445

Ser Pro Asn Thr Leu Asn Asn Gly Asn Pro Lys Gln Ala Asn Gln Thr
    450                 455                 460

Val Gly Asp Gly Phe Phe Thr Thr Pro Gly Arg Thr Thr Ser Gly Arg
465                 470                 475                 480

Leu Met Arg Thr Val Ser Ser Thr Phe Ser Asp Val Trp Ser Gln Pro
            485                 490                 495

Arg Leu Phe Tyr Asn Ser Leu Val Pro Ala Glu Gln Gln Phe Leu Val
        500                 505                 510

Asn Ala Ile Arg Phe Glu Asn Ser Asn Val Lys Ser Glu Val Val Arg
    515                 520                 525

Asn Asn Val Ile Ile Gln Leu Asn Arg Val Asp Asn Asp Leu Ala Arg
    530                 535                 540

Arg Val Ala Arg Val Ile Gly Val Ala Glu Pro Glu Pro Asp Pro Thr
545                 550                 555                 560

Tyr Tyr His Asn Asn Lys Thr Ala Asn Val Gly Thr Phe Gly Thr Pro
            565                 570                 575

Leu Lys Arg Ile Asp Gly Leu Lys Val Gly Val Leu Ala Thr Val Gly
        580                 585                 590

Asp Pro Asp Ser Ile Ser Gln Gly Gln Ser Leu Ser Asp Ala Leu Ser
    595                 600                 605

Asp Ser Lys Val Asp Val Thr Val Val Ala Glu Ser Phe Thr Asp Gly
    610                 615                 620

Val Asp Ala Leu Tyr Thr Asn Ser Asp Ala Thr Gly Phe Asp Ala Val
625                 630                 635                 640

Ile Val Ala Asp Gly Ala Glu Gly Leu Phe Thr Pro Ser Ser Phe Thr
            645                 650                 655

Ala Lys Pro Thr Asn Ser Phe Ser Thr Thr Thr Leu Tyr Pro Ala Gly
        660                 665                 670
```

Arg Pro Leu Gln Ile Leu Val Asp Ala Phe Arg Phe Gly Lys Pro Val
            675                 680                 685

Gly Ala Leu Gly Ser Gly Ala Lys Ala Leu Asp Ala Ala Gly Ile Ser
        690                 695                 700

Thr Ser Arg Pro Gly Val Tyr Val Ala Asn Ser Thr Ser Glu Ala Phe
705                 710                 715                 720

Thr Asp Asp Ile Glu Asp Gly Leu Arg Thr Phe Lys Phe Leu Asp Arg
            725                 730                 735

Phe Ala Leu Asp Glu
            740

<210> SEQ ID NO 9
<211> LENGTH: 37
<212> TYPE: DNA
<213> ORGANISM: Artificial Sequence
<220> FEATURE:
<223> OTHER INFORMATION: Synthetic Construct

<400> SEQUENCE: 9
acacaactgg ggatccacca tgccgaacct cgtacgg                              37

<210> SEQ ID NO 10
<211> LENGTH: 43
<212> TYPE: DNA
<213> ORGANISM: Artificial Sequence
<220> FEATURE:
<223> OTHER INFORMATION: Synthetic Construct

<400> SEQUENCE: 10
gtcaccctct agatctgaag gtgcactact gaccttacac gag                       43

<210> SEQ ID NO 11
<211> LENGTH: 40
<212> TYPE: DNA
<213> ORGANISM: Artificial Sequence
<220> FEATURE:
<223> OTHER INFORMATION: Synthetic Construct

<400> SEQUENCE: 11
acacaactgg ggatccacca tgcgactagg tgccttggca                           40

<210> SEQ ID NO 12
<211> LENGTH: 47
<212> TYPE: DNA
<213> ORGANISM: Artificial Sequence
<220> FEATURE:
<223> OTHER INFORMATION: Synthetic Construct

<400> SEQUENCE: 12
gtcaccctct agatctatcg attgagttgt acaagttcag ctacagc                   47

<210> SEQ ID NO 13
<211> LENGTH: 40
<212> TYPE: DNA
<213> ORGANISM: Artificial Sequence
<220> FEATURE:
<223> OTHER INFORMATION: Synthetic Construct

<400> SEQUENCE: 13
acacaactgg ggatccacca tgaaagccgg ttcgcttctc                           40

```
<210> SEQ ID NO 14
<211> LENGTH: 46
<212> TYPE: DNA
<213> ORGANISM: Artificial Sequence
<220> FEATURE:
<223> OTHER INFORMATION: Synthetic Construct

<400> SEQUENCE: 14
gtcaccctct agatctcata tacgtaggac tgggatgata actgtg          46

<210> SEQ ID NO 15
<211> LENGTH: 36
<212> TYPE: DNA
<213> ORGANISM: Artificial Sequence
<220> FEATURE:
<223> OTHER INFORMATION: Synthetic Construct

<400> SEQUENCE: 15
acacaactgg ggatccacca tgcgcgcagt gcagct                     36

<210> SEQ ID NO 16
<211> LENGTH: 47
<212> TYPE: DNA
<213> ORGANISM: Artificial Sequence
<220> FEATURE:
<223> OTHER INFORMATION: Synthetic Construct

<400> SEQUENCE: 16
gtcaccctct agatctgtcg actattccaa ccttcctata tggacac         47
```